(12) United States Patent
Sarrafzadeh et al.

(10) Patent No.: US 9,888,868 B2
(45) Date of Patent: Feb. 13, 2018

(54) ENERGY AWARE SENSOR MANAGEMENT FOR WEARABLE MEDICAL SYSTEMS OPTIMIZATION

(75) Inventors: Majid Sarrafzadeh, Anaheim Hills, CA (US); Miodrag Potkonjak, Los Angeles, CA (US); Foad Dabiri, San Francisco, CA (US); Hyduke Noshadi, Sherman Oaks, CA (US); Saro Meguerdichian, West Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 356 days.

(21) Appl. No.: 13/704,945

(22) PCT Filed: Jun. 17, 2011

(86) PCT No.: PCT/US2011/040910
§ 371 (c)(1),
(2), (4) Date: Dec. 17, 2012

(87) PCT Pub. No.: WO2011/160036
PCT Pub. Date: Dec. 22, 2011

(65) Prior Publication Data
US 2013/0096466 A1    Apr. 18, 2013

Related U.S. Application Data

(60) Provisional application No. 61/355,944, filed on Jun. 17, 2010.

(51) Int. Cl.
*A61B 5/103*    (2006.01)
*A61B 5/00*    (2006.01)

(52) U.S. Cl.
CPC .......... *A61B 5/1038* (2013.01); *A61B 5/0004* (2013.01); *A61B 5/6807* (2013.01);
(Continued)

(58) Field of Classification Search
CPC ... A61B 5/0004; A61B 5/1036; A61B 5/1038; A61B 5/6807; A61B 5/7285;
(Continued)

(56) References Cited

U.S. PATENT DOCUMENTS 6,493,652 B1 * 12/2002 Ohlenbusch et al. ........ 702/160
8,231,555 B2 *  7/2012 Skelton et al. ............... 600/595
(Continued)

OTHER PUBLICATIONS

Bamberg et al. "Gait analysis using a shoe-integrated wireless sensor system." Information Technology in Biomedicine, IEEE Transactions on 12(4) (2008): 413-423.*
(Continued)

*Primary Examiner* — David J McCrosky
(74) *Attorney, Agent, or Firm* — Foley & Lardner LLP; Cliff Z. Liu

(57) ABSTRACT

A sensor system and method configured to take multiple channels of sensors, and based on context and user behavior reflected in the signals, identifies specified channels for sensing according to a sensing policy. The sensing policy is used to reduce the amount of data sampled, such that it is possible to reconstruct the values of the non sampled sensors efficiently. The sensing policy is influenced by user and system's behavior and can be assigned either offline or in real time.

11 Claims, 29 Drawing Sheets

(52) U.S. Cl.
CPC .......... *A61B 5/7225* (2013.01); *A61B 5/6829* (2013.01); *A61B 5/7271* (2013.01)

(58) Field of Classification Search
CPC ..... A61B 5/7271; A61B 5/6829; A61B 5/112; A43B 3/0005; G08B 21/0446; G08B 21/0453; Y10S 128/903
USPC .......... 600/300, 301, 587, 592, 595; 702/138–142, 150, 160, 173, 175, 189; 700/28–55; 713/310, 320–324; 128/903; 307/140, 141
See application file for complete search history.

(56) References Cited

U.S. PATENT DOCUMENTS

| | | | | |
|---|---|---|---|---|
| 8,676,541 | B2* | 3/2014 | Schrock | A43B 3/0005 702/188 |
| 2001/0047127 | A1 | 11/2001 | New et al. | |
| 2006/0080551 | A1* | 4/2006 | Mantyjarvi et al. | 713/186 |
| 2006/0094968 | A1 | 5/2006 | Drew et al. | |
| 2006/0202816 | A1 | 9/2006 | Crump et al. | |
| 2009/0076343 | A1 | 3/2009 | James et al. | |
| 2009/0278707 | A1* | 11/2009 | Biggins et al. | 340/870.16 |
| 2011/0152727 | A1* | 6/2011 | Ten Kate | 600/595 |

OTHER PUBLICATIONS

Koushanfar et al. "Sleeping Coordination for Comprehensive Sensing Using Isotonic Regression and Domatic Partitions." INFOCOM 2006. 25th IEEE International Conference on Computer Communications. Proceedings. IEEE, 2006.*
Noshadi, Hyduke. 2012. "Behavior-Aware Design, Optimization and Information Mining in Wearable Sensing Systems." Order No. 3509460, University of California, Los Angeles. pp. 5-8,42-45,79-81,104-112. Retrieved from <http://search.proquest.com/docview/1019809205?accountid=14753> on Dec. 31, 2014.*
Dabiri, Foad. 2008. "Wireless Health: Reliability Oriented Design and Optimization." Order No. 3347021, University of California, Los Angeles. Abstract. Retrieved from <http://search.proquest.com/docview/304661838?accountid=14753> on Dec. 31, 2014.*
Mutual. Dictionary.com. Dictionary.com Unabridged. Random House, Inc. http://dictionary.reference.com/browse/mutual (accessed: Dec. 31, 2014).*
Bronzino, Joseph D. (2006). Biomedical Engineering Handbook—Biomedical Engineering Fundamentals (3rd Edition). Taylor & Francis. vol. 2, Sect. 1.12. Retrieved from <http://app.knovel.com/hotlink/toc/id:kpBEHBEFE4/biomedical-engineering/biomedical-engineering> on Dec. 31, 2014.*
Zappi, et al. "Activity recognition from on-body sensors: accuracy-power trade-off by dynamic sensor selection." Wireless Sensor Networks. Springer Berlin Heidelberg, 2008. 17-33.*
PCTUS2011/040910. Int'l Search Report & Written Opinion dated Feb. 9, 2012.

* cited by examiner

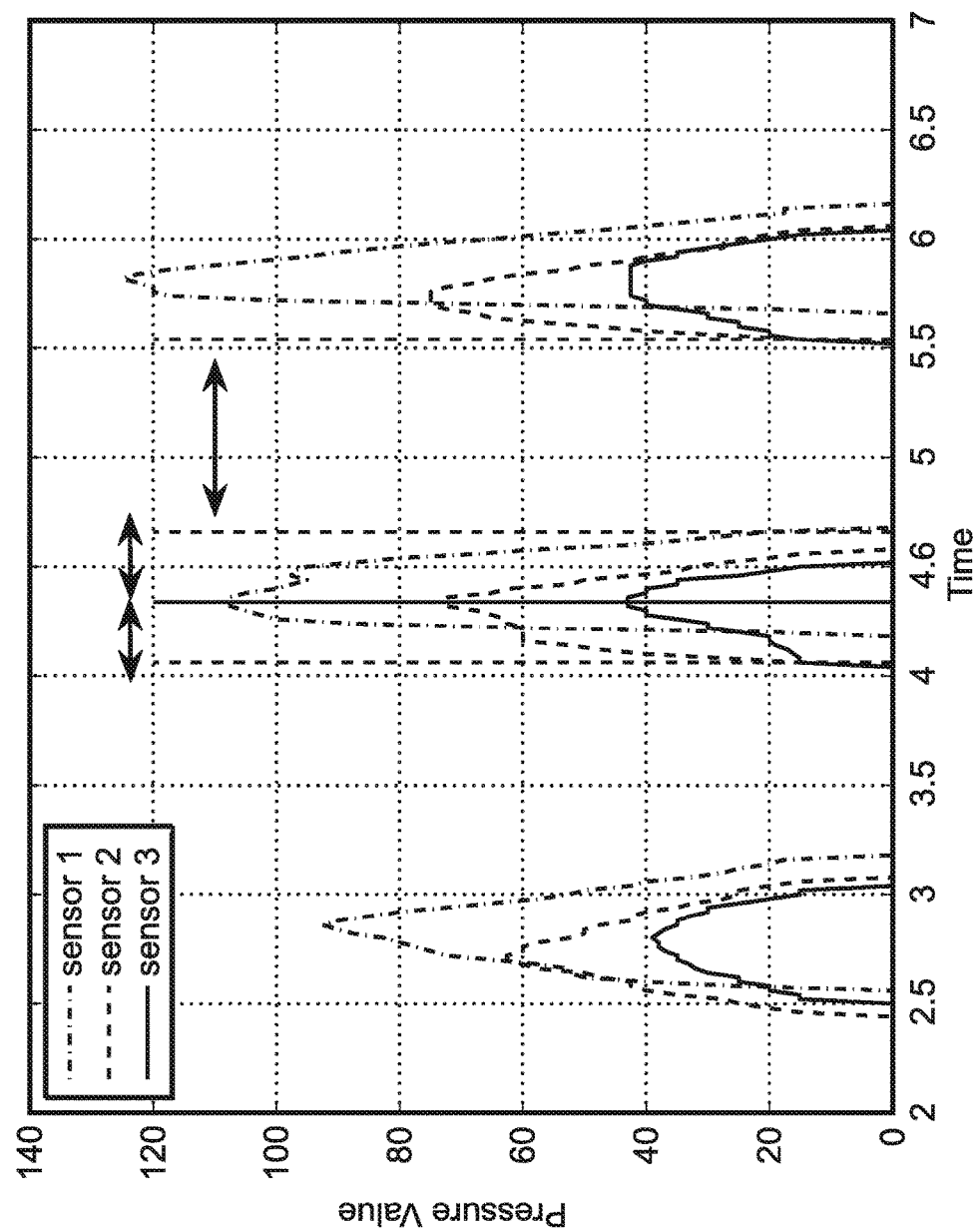

ENERGY AWARE SENSOR MANAGEMENT FOR WEARABLE MEDICAL SYSTEMS OPTIMIZATION

CROSS-REFERENCE TO RELATED APPLICATIONS

This application is a National Stage Entry of PCT/US2011/040910, filed Jun. 17, 2011, which claims the benefit of U.S. provisional patent application Ser. No. 61/355,944 filed on Jun. 17, 2010, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to a sensor system, and more particularly to a sensor system for sensing physiological characteristics.

2. Description of Related Art

Wearable sensing systems are becoming widely used for a variety of applications, including sports, entertainment, and military. These systems have recently enabled a variety of medical monitoring and diagnostic applications in wireless health.

Embedded networked systems and wide area cellular wireless systems are becoming ubiquitous in applications ranging from environmental monitoring to urban sensing Meanwhile, sensor networks have emerged as an important class of distributed embedded systems capable of solving a variety of challenging monitoring and control problems in a number of application domains, ranging from government and military applications to seismic, habitat, and wildlife continuous observations. These technologies have recently been adopted to support the emerging work in medical devices equipped with sensors Some wearable systems have been proposed for monitoring the athletic performance in a variety of sports such as skiing, baseball, martial arts, tennis, and golf. These systems are mainly designed for short term use during training sessions.

However, the need for multiple sensors and constant monitoring leads these systems to be power hungry and expensive, with short operating lifetimes.

Accordingly, an object of the present invention is a sensor system configured to minimize data received from a multiple-sensor array, while maintaining the integrity of the original signal. At least some of these objectives will be met in the description below.

BRIEF SUMMARY OF THE INVENTION

An aspect of the present invention is a system which takes multiple channels of sensors, and based on context and user behavior, which is reflected in the signals, identifies specified channels for sensing and a sensing policy. The sensing policy is used to reduce the amount of data sampled, such that it is possible to reconstruct the values of the non sampled sensors efficiently. The sensing policy is influenced by user and system's behavior and can be assigned either offline or in real time.

The systems and methods of the present invention use contextual and semantic properties in human behavior to enable efficient design and optimization of sensor systems from the data and information point of view. This, in turn, directly influences the wireless communication and local processing power consumption of the system. Intrinsic space and temporal correlations between sensor data are used, while considering both user and system contextual behavior. The primary focus of the system and methods of the present invention is to take data from a small subset of sensors to accurately capture and/or predict all possible signals of a fully instrumented wearable sensing system. The systems and methods of the present invention use modeling, partitioning, and behavioral optimization, which consists of signal characterization, segmentation and time shifting, mutual signal prediction, and a simultaneous minimization composed of subset sensor selection.

Furthermore, opportunistic sampling is used, which selects a small subset of sensors which can predict when to control sampling of the rest of the network.

The systems and methods of the present invention use signal processing techniques: time-shifting, segmentation, and adaptive opportunistic sampling, etc., in addition to a new combinatorial optimization paradigm (pseudo-exhaustive combinatorial search), to design a sensor policy for an energy optimized embedded sensing system that is capable of reducing energy consumption by more than an order of magnitude. While some of methods of the present invention best perform on embedded sensing systems that share local communication, a majority of them can be applied on essentially any sensing system with intrinsic behavioral properties.

With the systems and methods of the present invention, previously expensive wearable sensing systems used in medical studies can be made more attractive to daily usage through a system of coordinated design and operational techniques that facilitate mass production, customization to specific customers, and low power operation.

Specifically, the systems and methods of the present invention simultaneously minimize the cost (i.e. the number of sensors) and energy consumption (i.e. the weighted sum of collected and communicated samples), while preserving a specified accuracy of collected data, or vice versa. Wireless communication energy consumption, rather than signal sensing energy, is the primary focus, since sensing energy consumption is negligible compared to that of wireless communication. Intrinsic space and temporal correlations are exploited between sensor data, while considering both user and system behavior.

The systems and methods of the present invention use signal semantics and predictability among sensors to reduce the number of sensors and amount of data acquisition, and in particular use several signal evaluation/processing techniques.

A first aspect is signal time-shifting, wherein a binary search can be used for very fast calculation of the best shifts (based on the observation is that cross-correlation functions are almost always unimodular). In addition, the complexity of the sensor selection problem does not increase since the selected signals can be shifted by any required amount.

Another aspect is signal segmentation for mutual sensor prediction. Signals in many types of embedded sensing systems have natural phases. For example: temperature and humidity are often highly impacted by sun activity, which is composed of morning, afternoon, and night phases; a heart beat has systolic and diastolic phases; and shoe pressure sensors are subject to airborne, landing, and take-off phases. Once the signals are aligned using signal time-shifting, the prediction of signals in each phase is much more accurate after segmentation, because data in one segment will otherwise often act as noise for data in another.

Yet another aspect is subset node selection. The selection of subsets of sensors from which the values of all other sensors can be computed within a given error can be mapped to the dominating set problem. A novel constructive algorithm (Combinatorial iterative component assembly (CICA)) may be used to facilitate an easy trade-off between the quality of the solution and the run time. CICA iteratively builds a number of partial solutions that are likely to be part of the final solution. An arbitrarily close approximation can be achieved at the expense of run time.

A further aspect is opportunistic sampling: The time-shifted nature of signals is also a basis for opportunistic sampling, where a small subset of sensors is regularly sampled while other sensors are placed in sleep mode. Sampling sensors in sleep mode is adaptively controlled by active sensors and data collection starts based on certain event detection by the active sensors. For example, the length of the airborne phase or when a person is standing still may be used for significant reduction in sensor sampling to achieve energy savings Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 6:
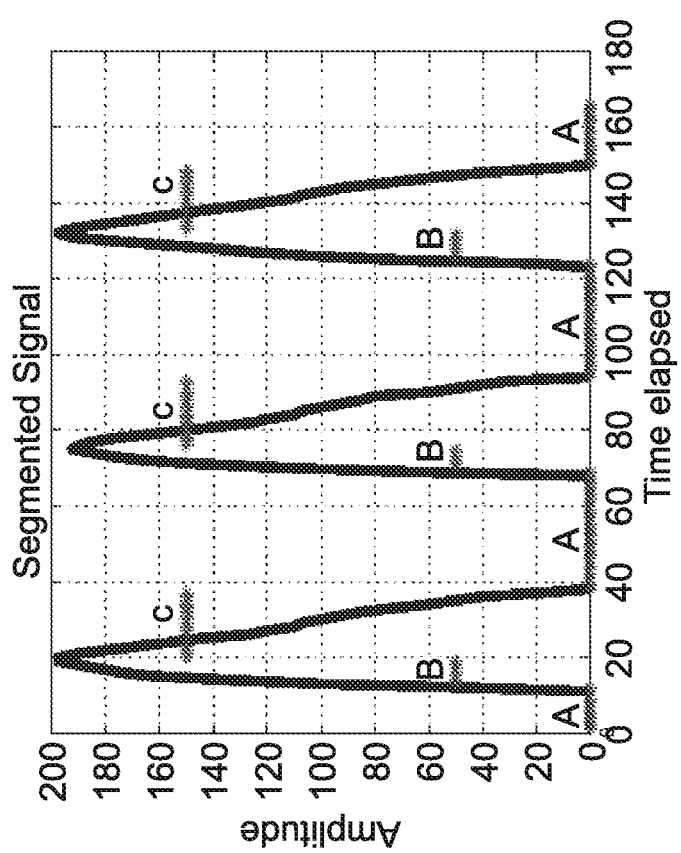

FIG. 6 demonstrates the extracted segments in the plantar pressure signal, (A) airborne, (B) take-off and (C) landing.

Figure 7:
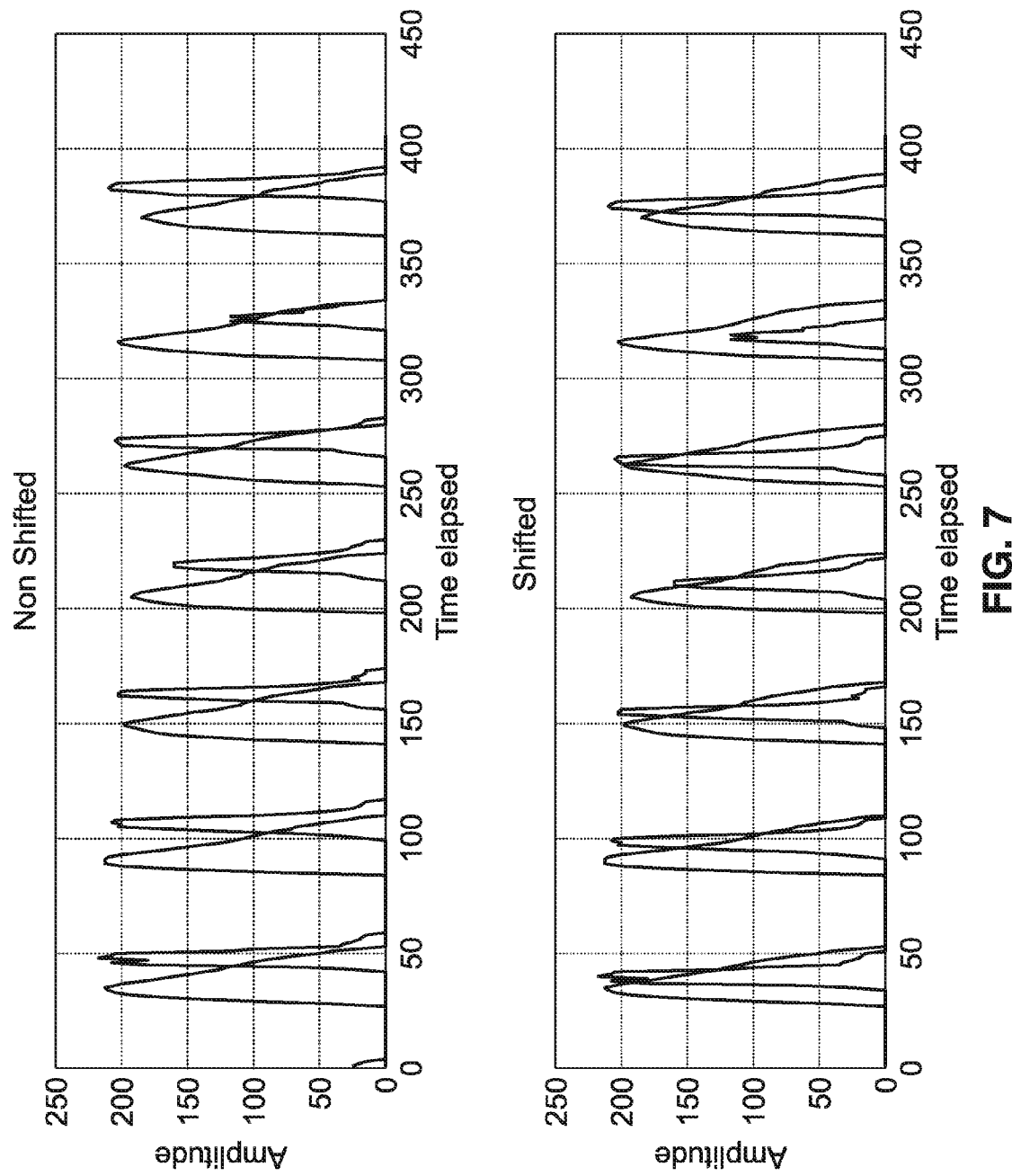

FIG. 7 shows plots of two signals at their original times and when one is shifted toward the other.

Figure 3:
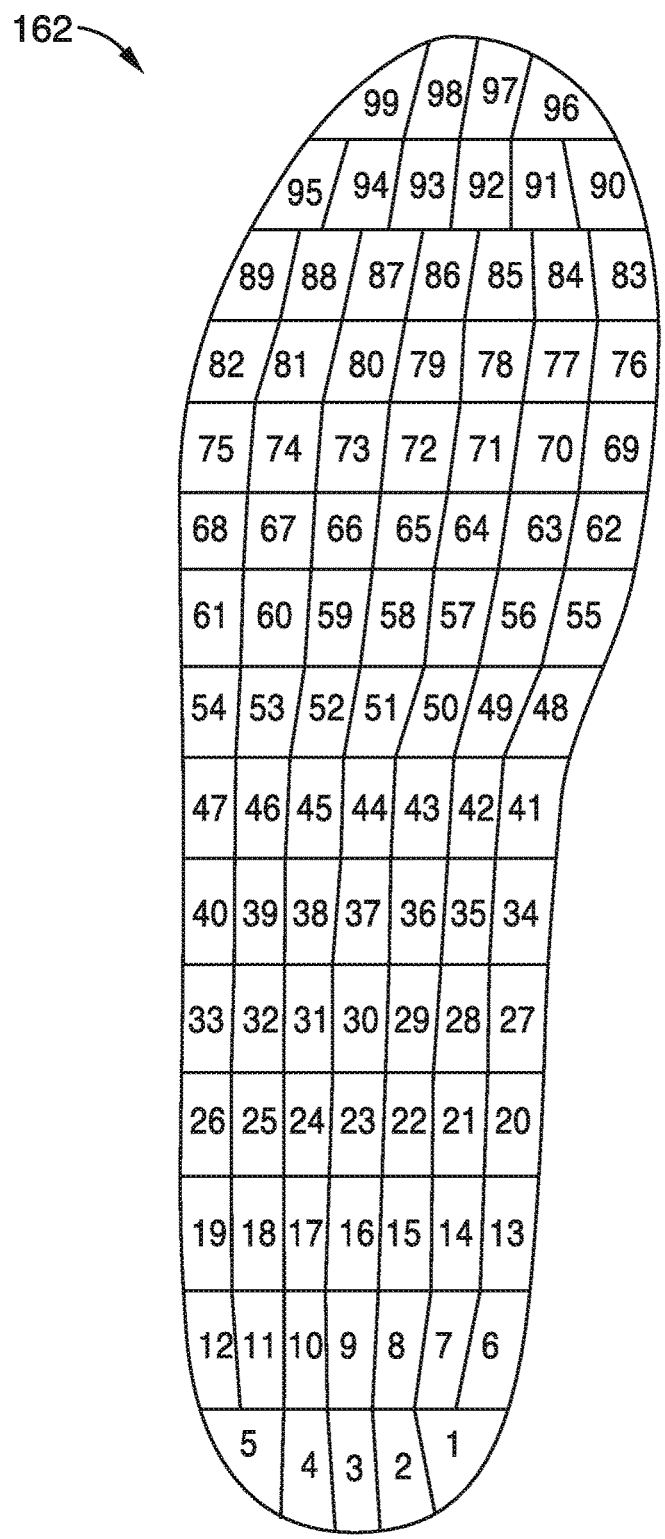
FIG. 3 shows a pressure sensor location map for a Pedar insole.
Figure 8A:
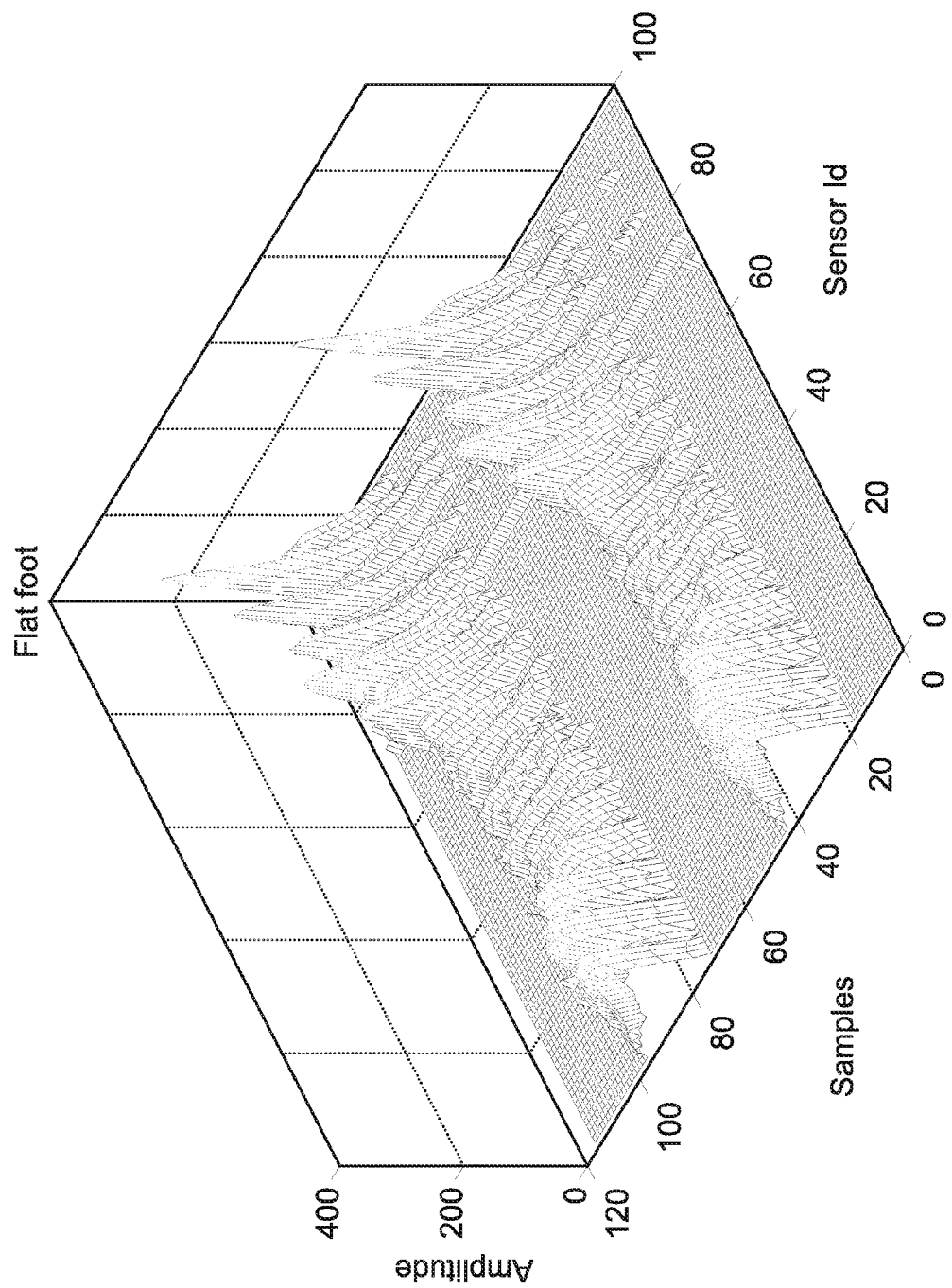
Figure 8B:
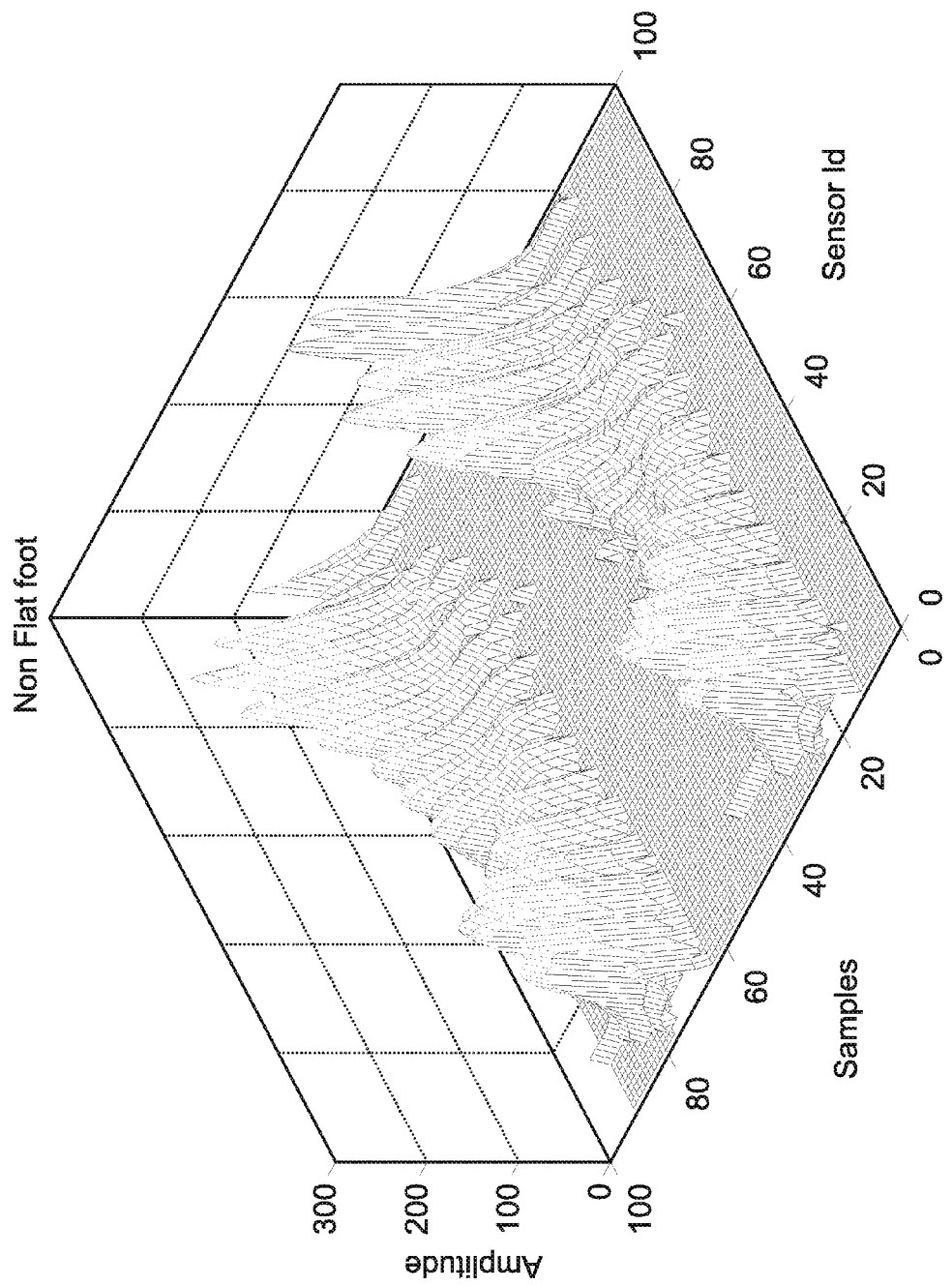

FIG. 8A and FIG. 8B show pressure readings from the Pedar sensor array of FIG. 3 for two test subjects.

Figure 9A:
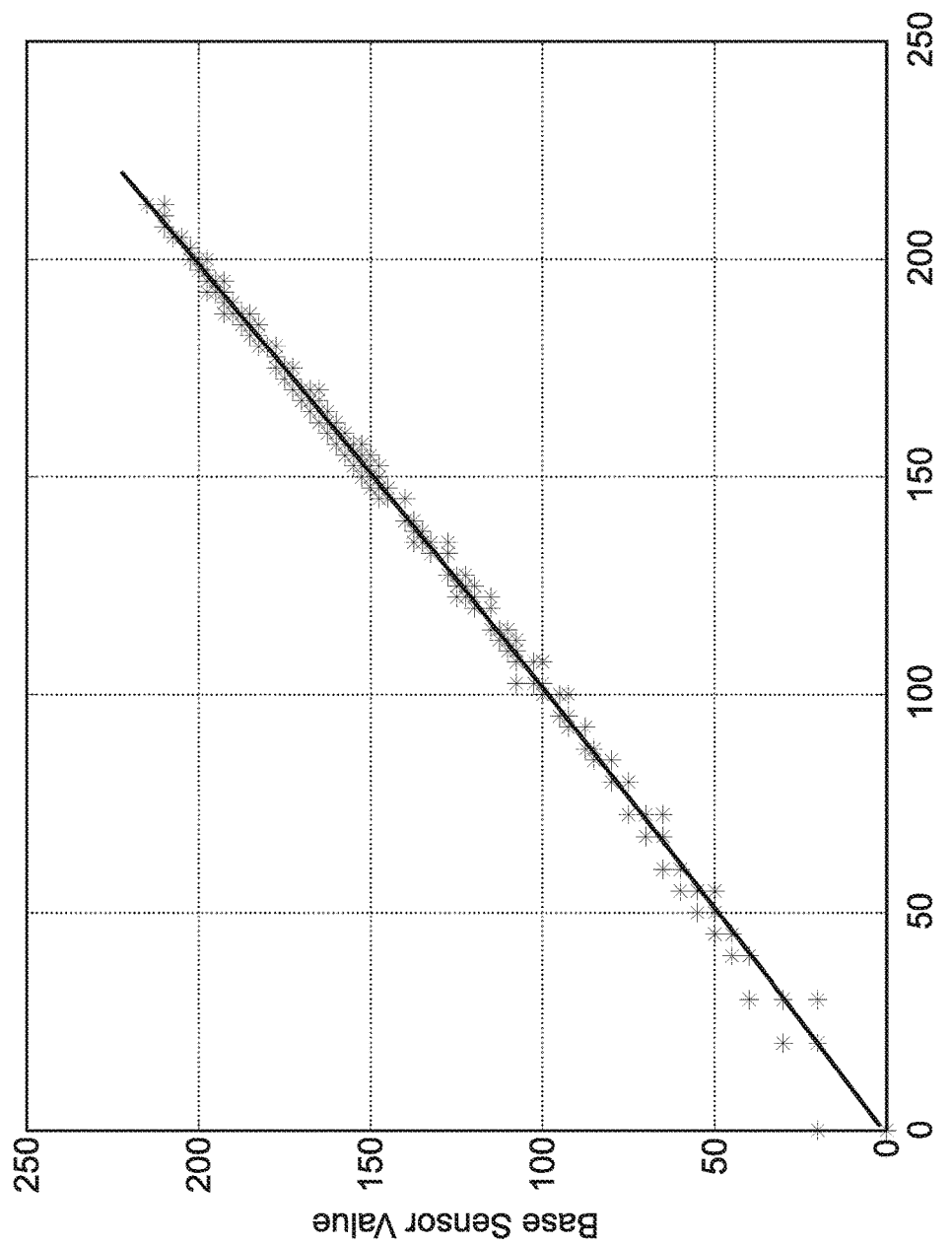
Figure 9B:
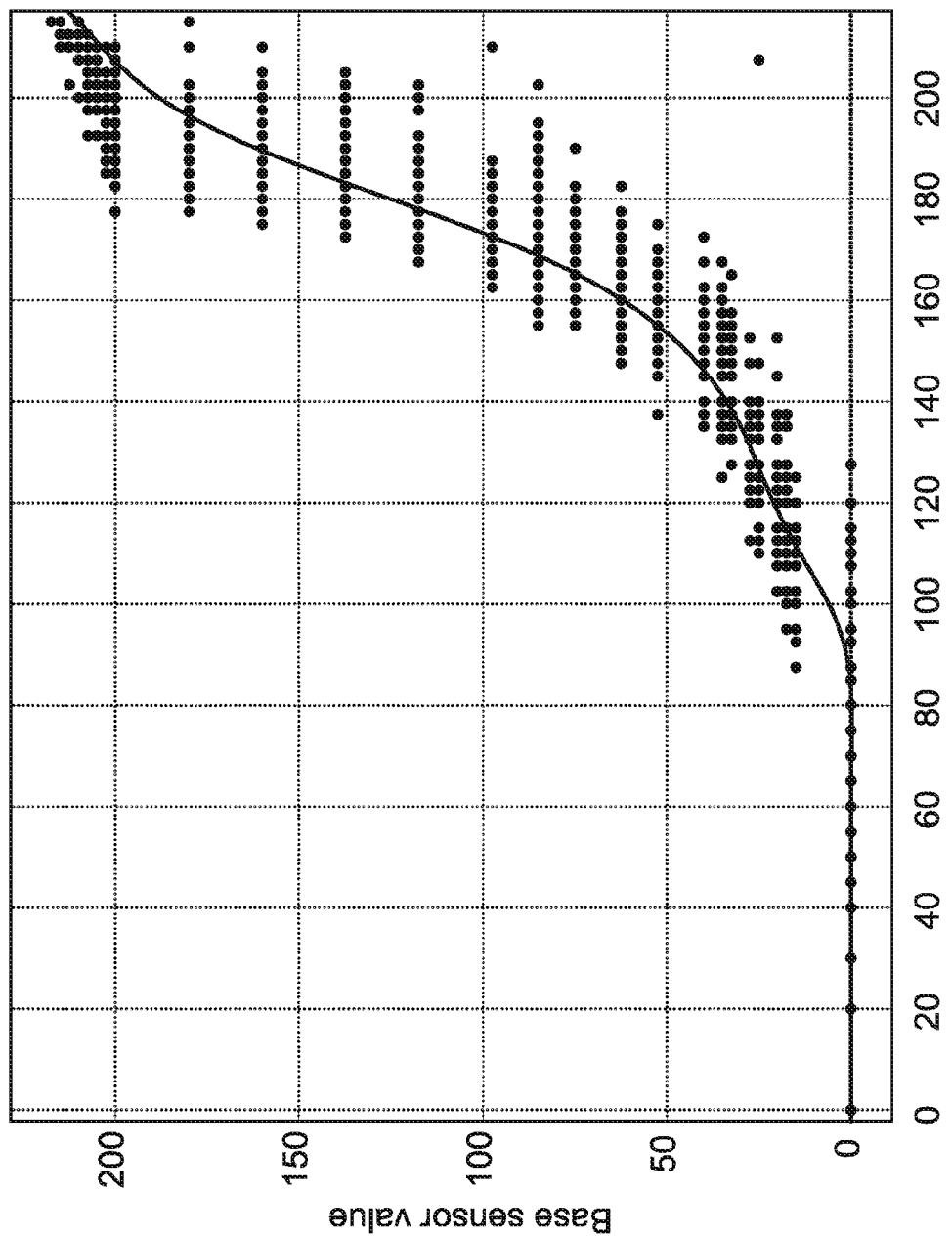
Figure 9C:
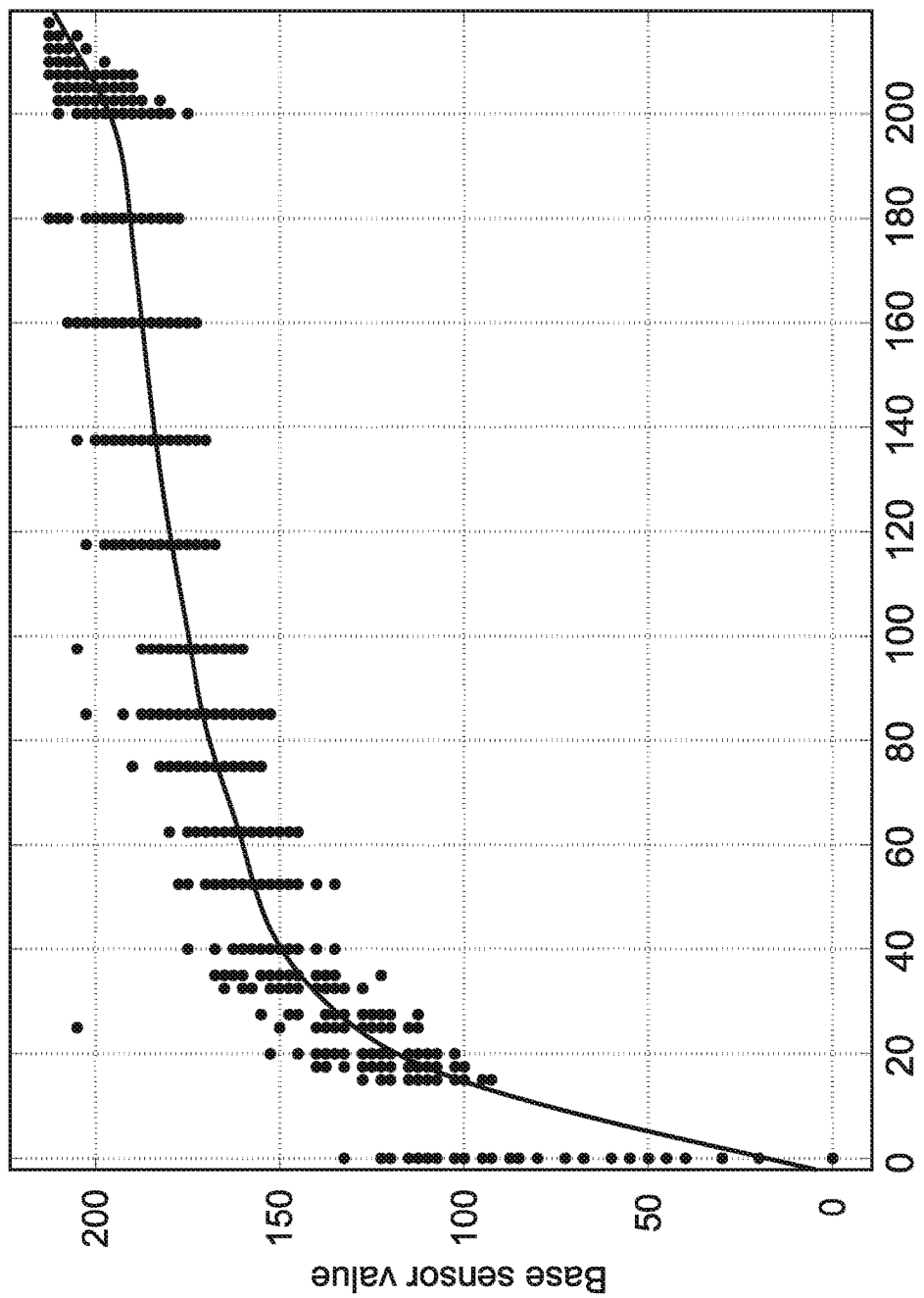

FIG. 9A, FIG. 9B, and FIG. 9C demonstrate fitted linear curves and isotonic curves, which illustrate the mathematical relationship between values from two different pairs of sensors.

Figure 10:
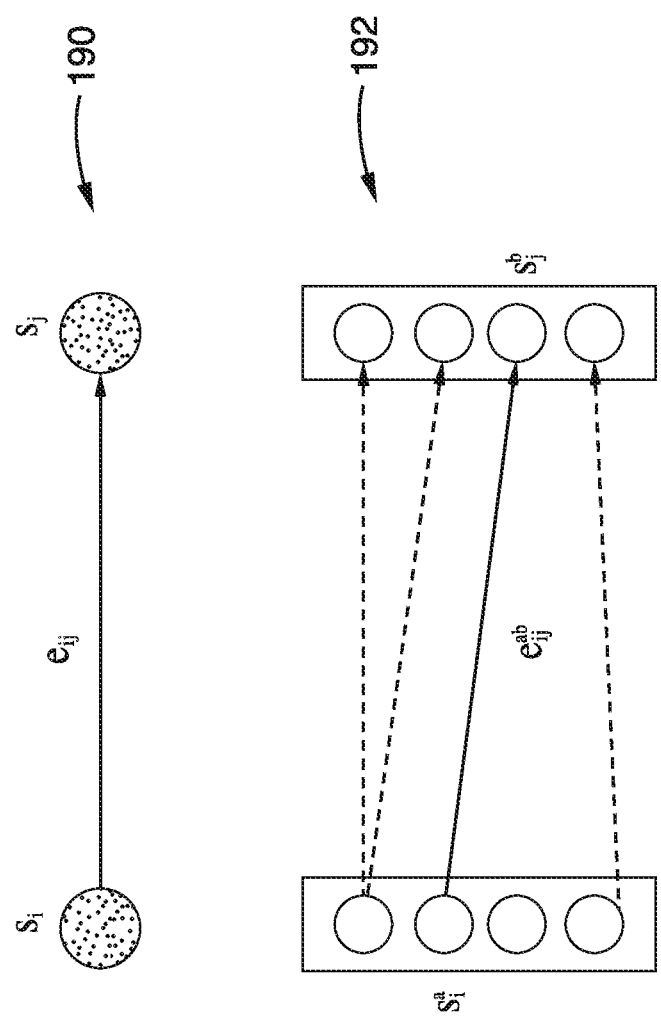

FIG. 10 is a graph of the comparison between TPSP vs. the single prediction method.

Figure 11A:
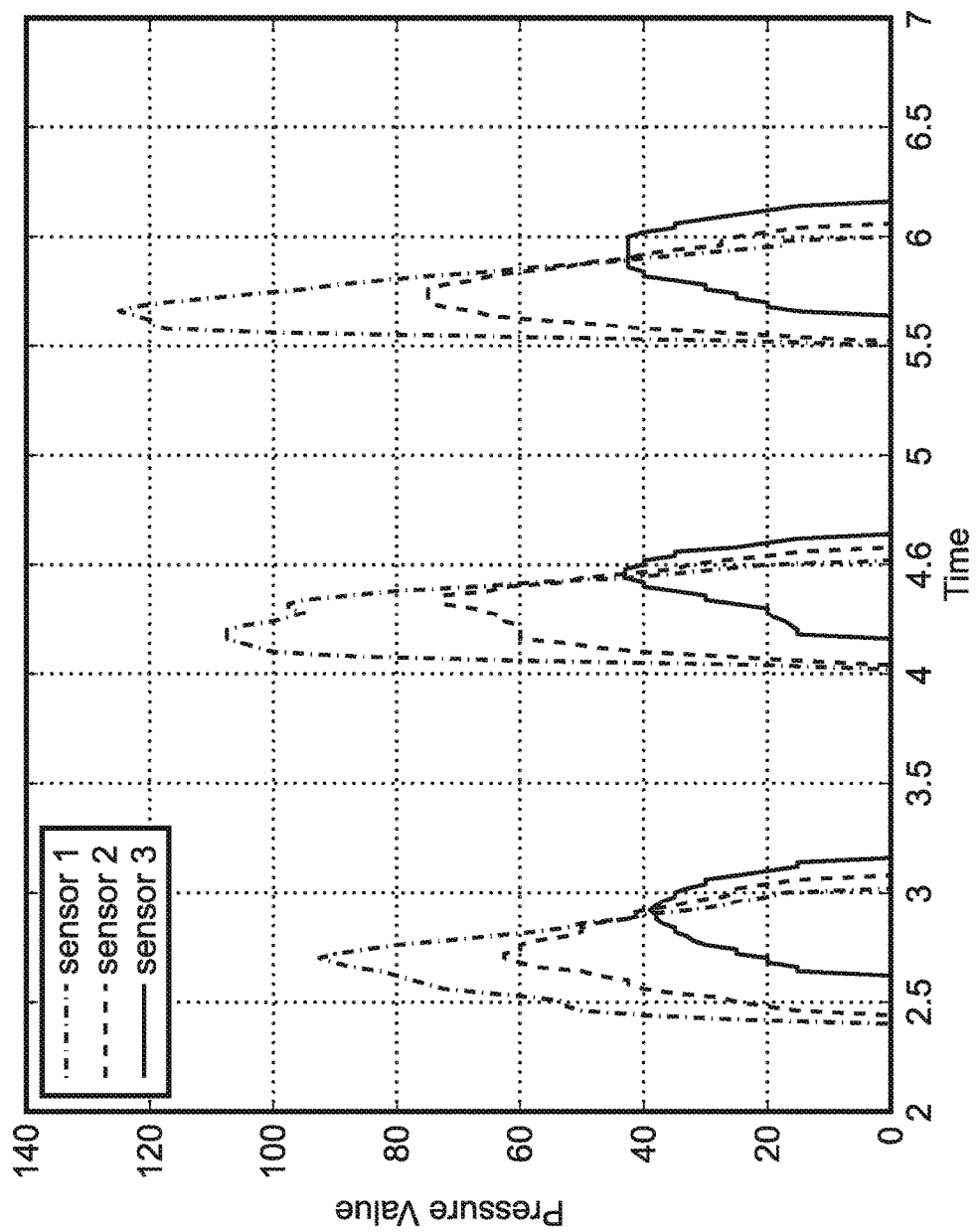

FIG. 11A and FIG. 11B show raw pressure patterns from three sensors (FIG. 11A) and after time-shift normalization (FIG. 11B).

Figure 12:

FIG. 12 is a flow diagram of a method for generating the elements in $\Phi$ matrix.

Figure 13:
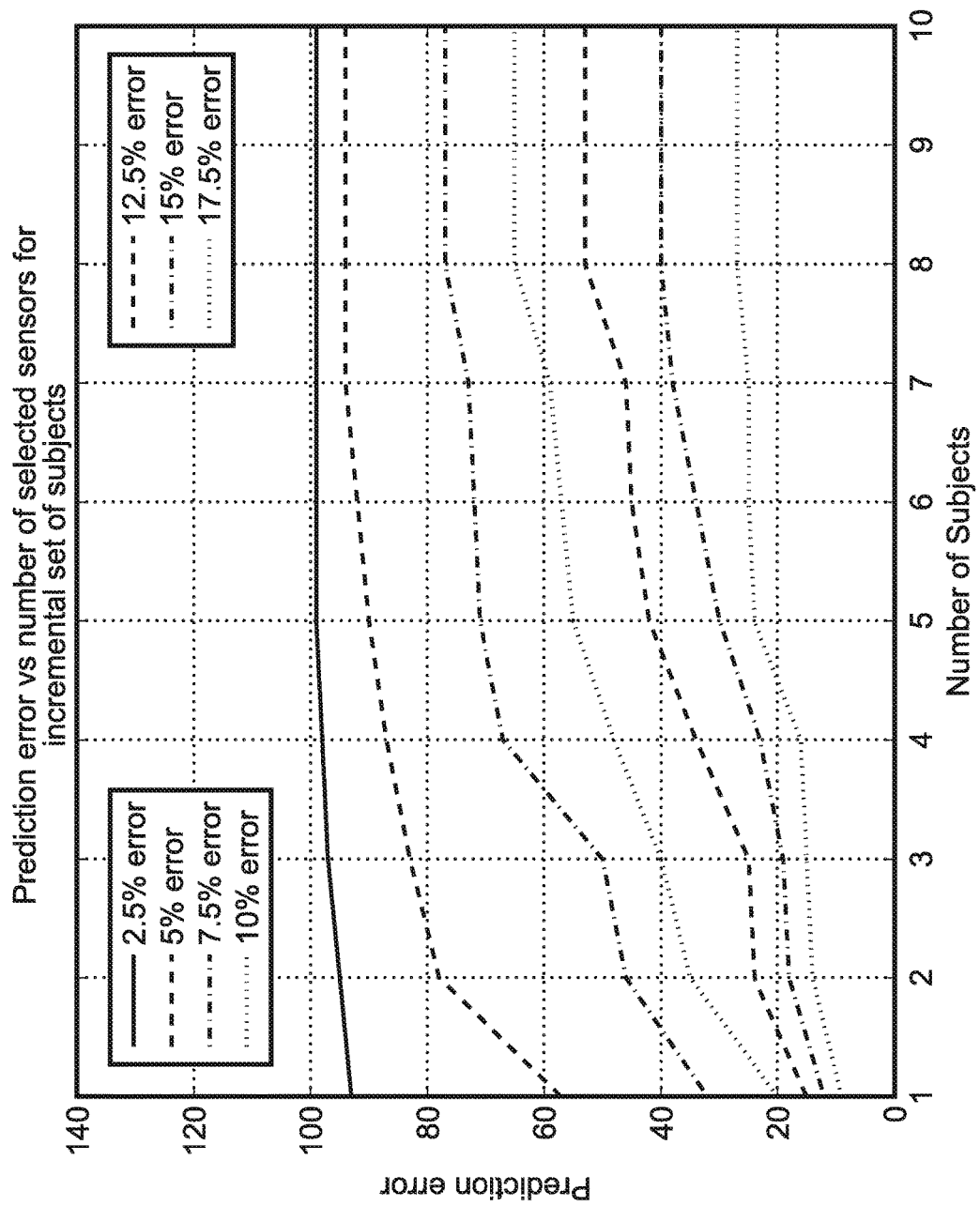

FIG. 13 shows the number of predictors for various numbers of test subjects and error rate bounds.

Figure 14:
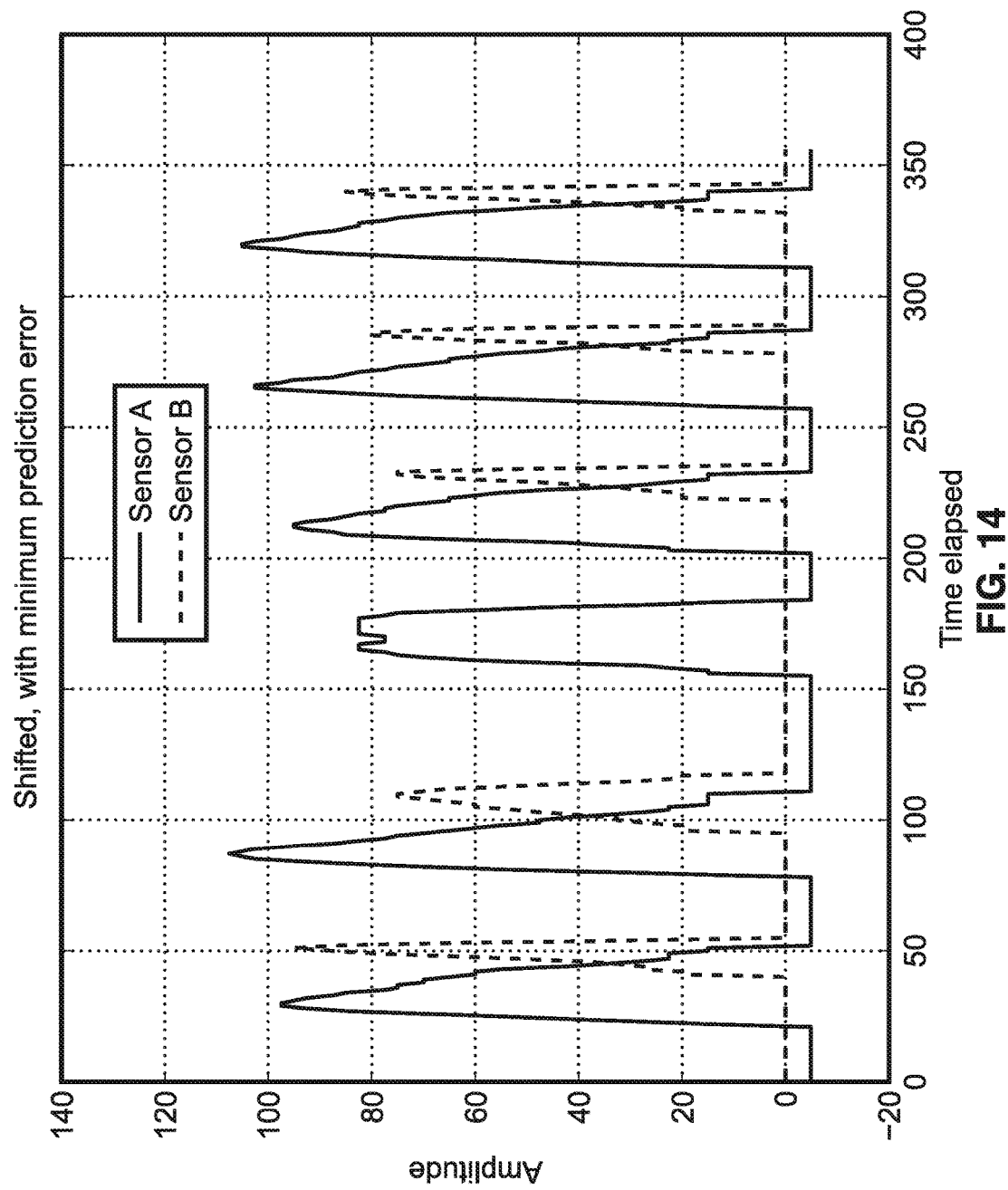

FIG. 14 illustrates precedence and triggering for two sensors.

Figure 15:
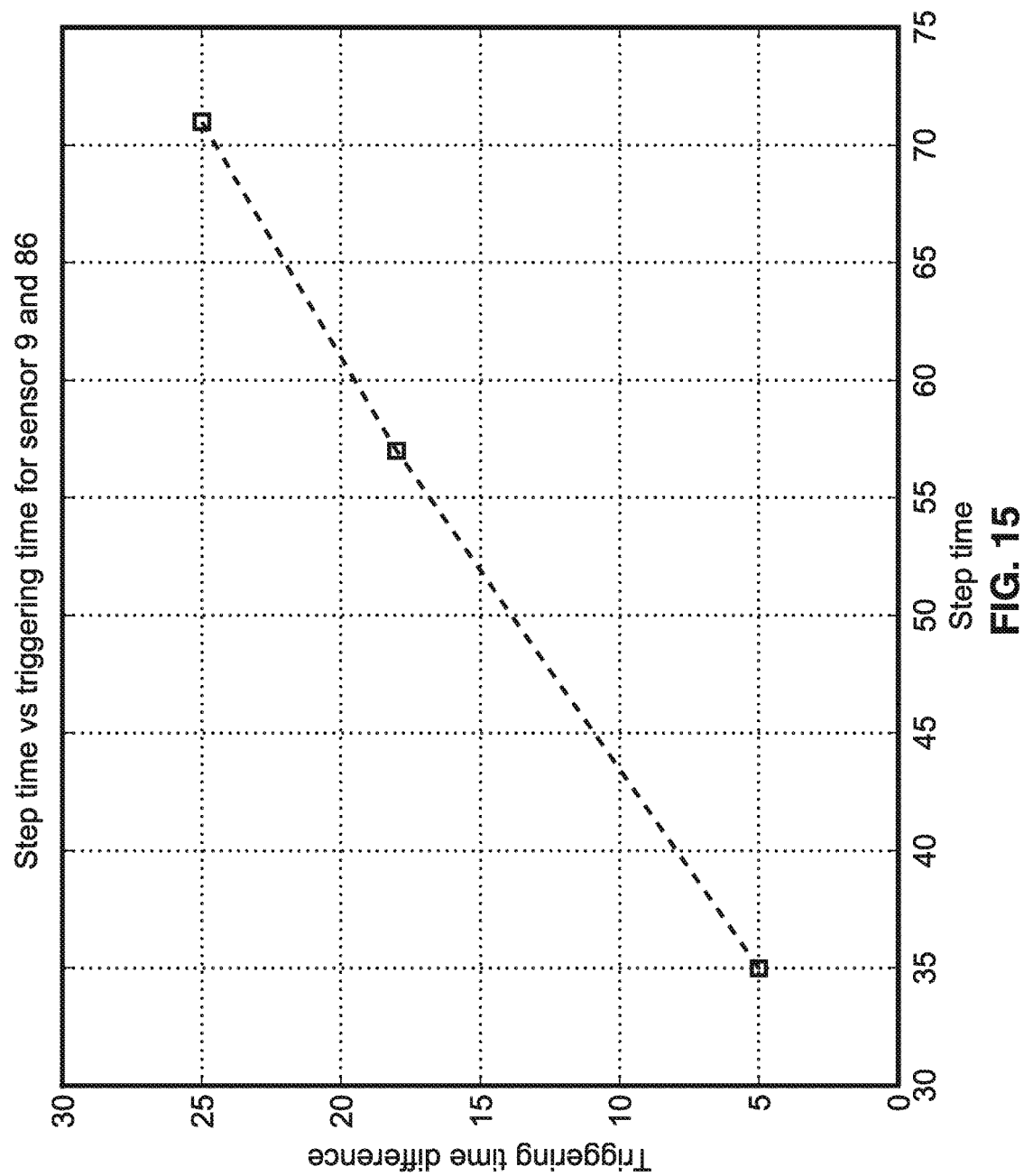

FIG. 15 shows the linear relationship of triggering distance to step time.

Figure 16B:
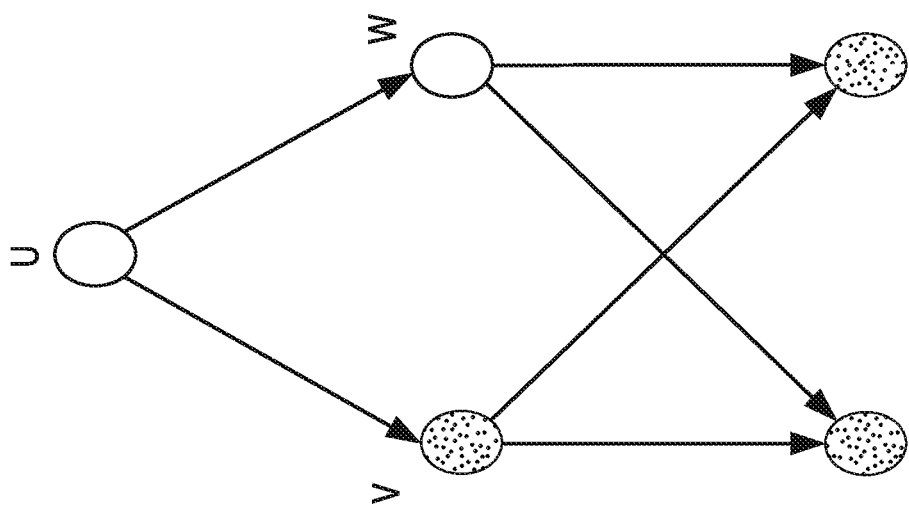
Figure 16A:
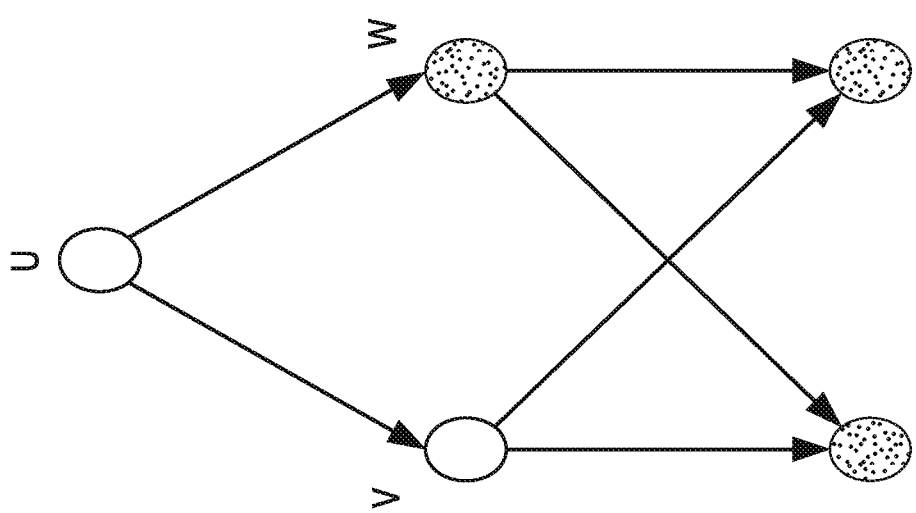

FIG. 16A and FIG. 16B illustrate an example of a triggering graph for a set of 5 sensors and two possible selection scenarios.

Figure 17A:
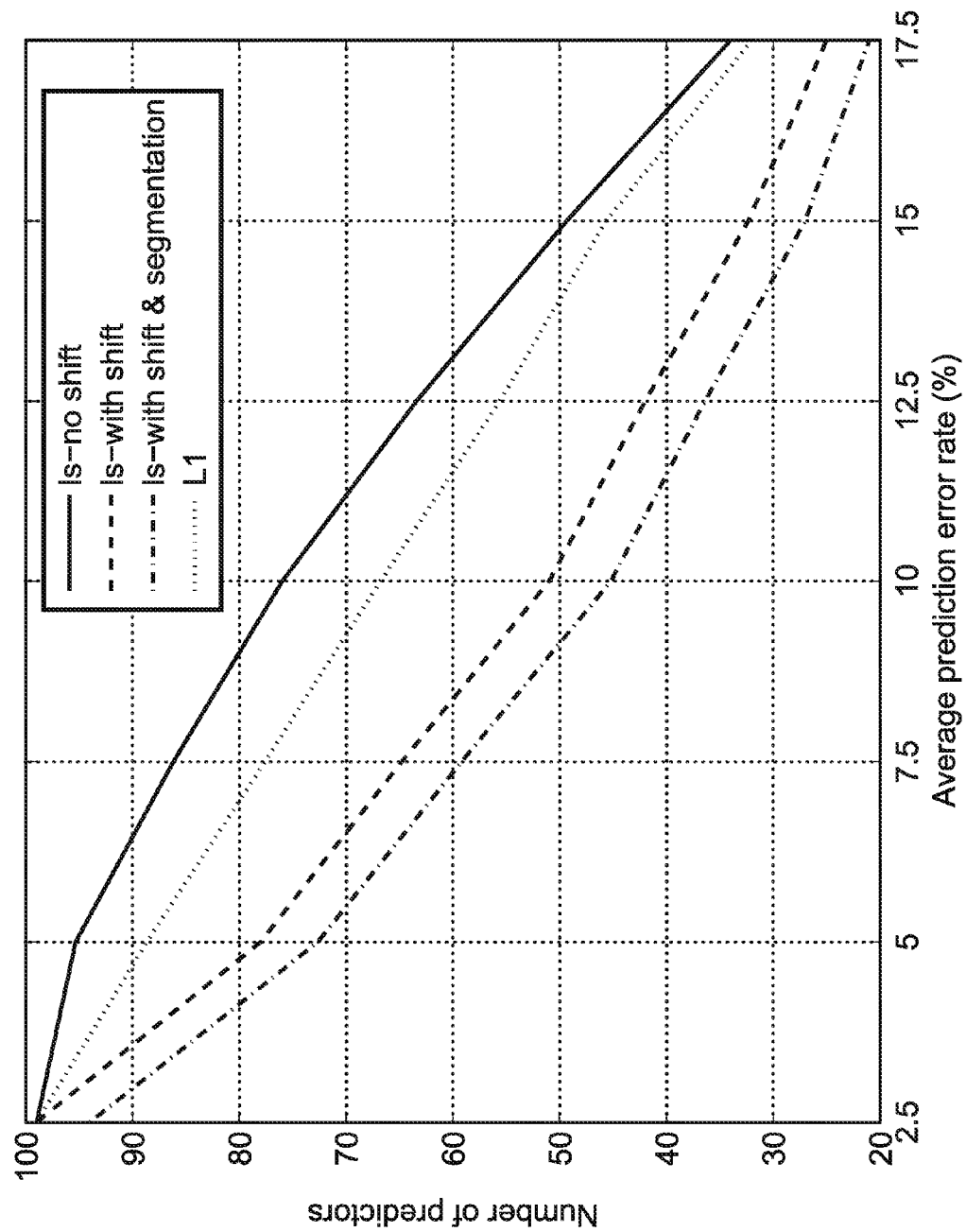
Figure 17B:
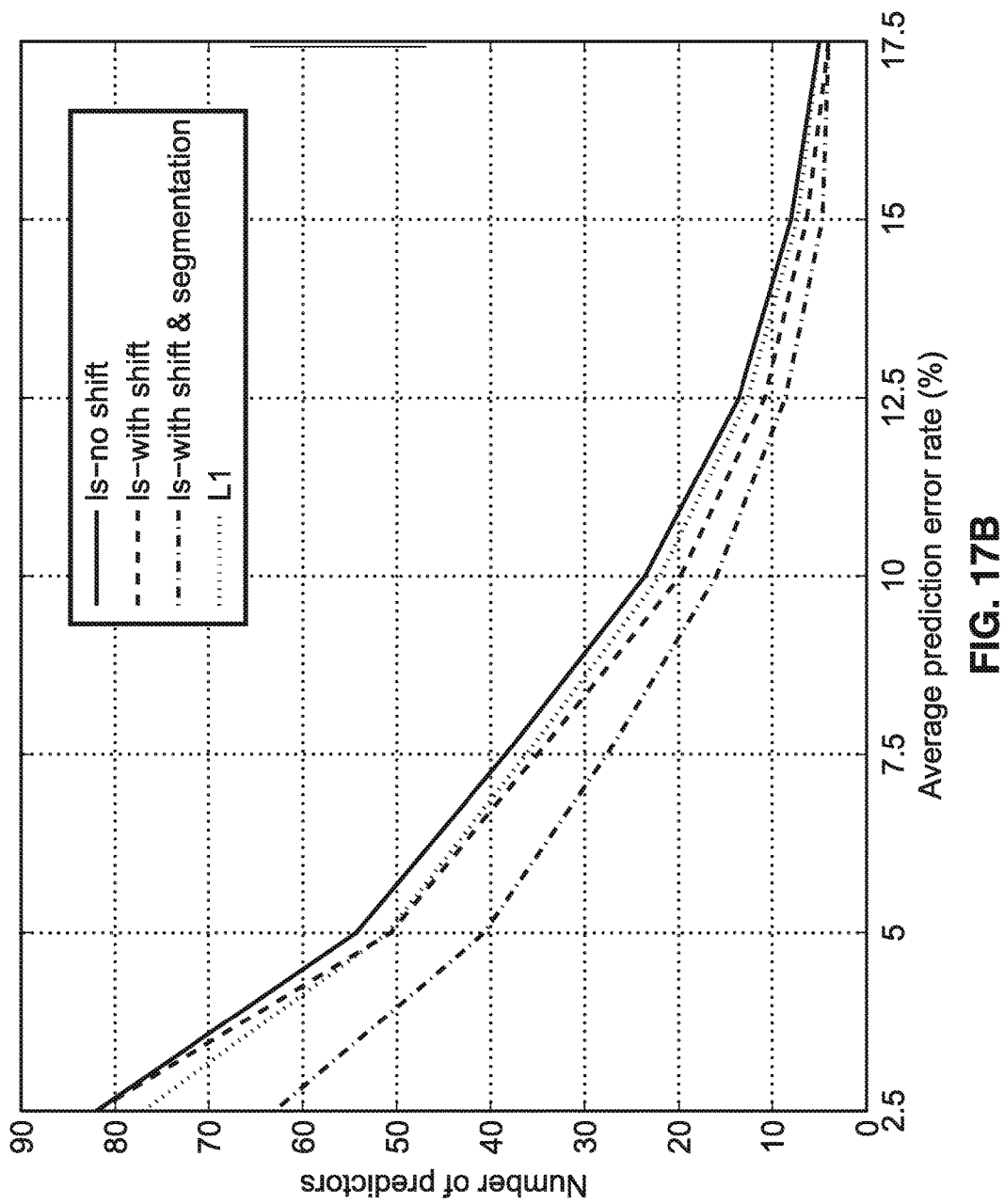

FIG. 17A and FIG. 17B show the number of predictor sensors vs. the average prediction error for the whole sensing network for (A) the general case and (B) averaged over individual test subjects.

Figure 18A:
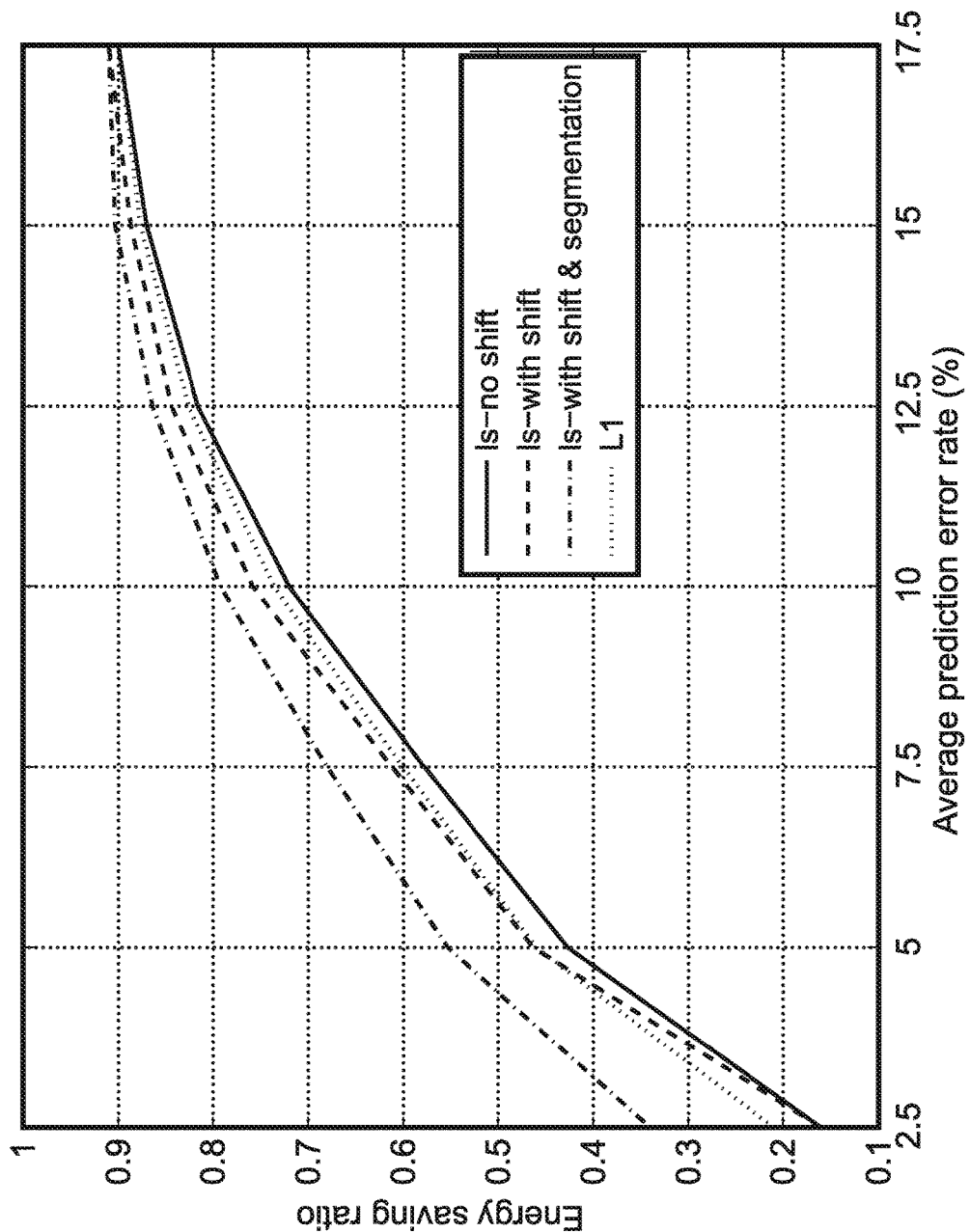
Figure 18B:
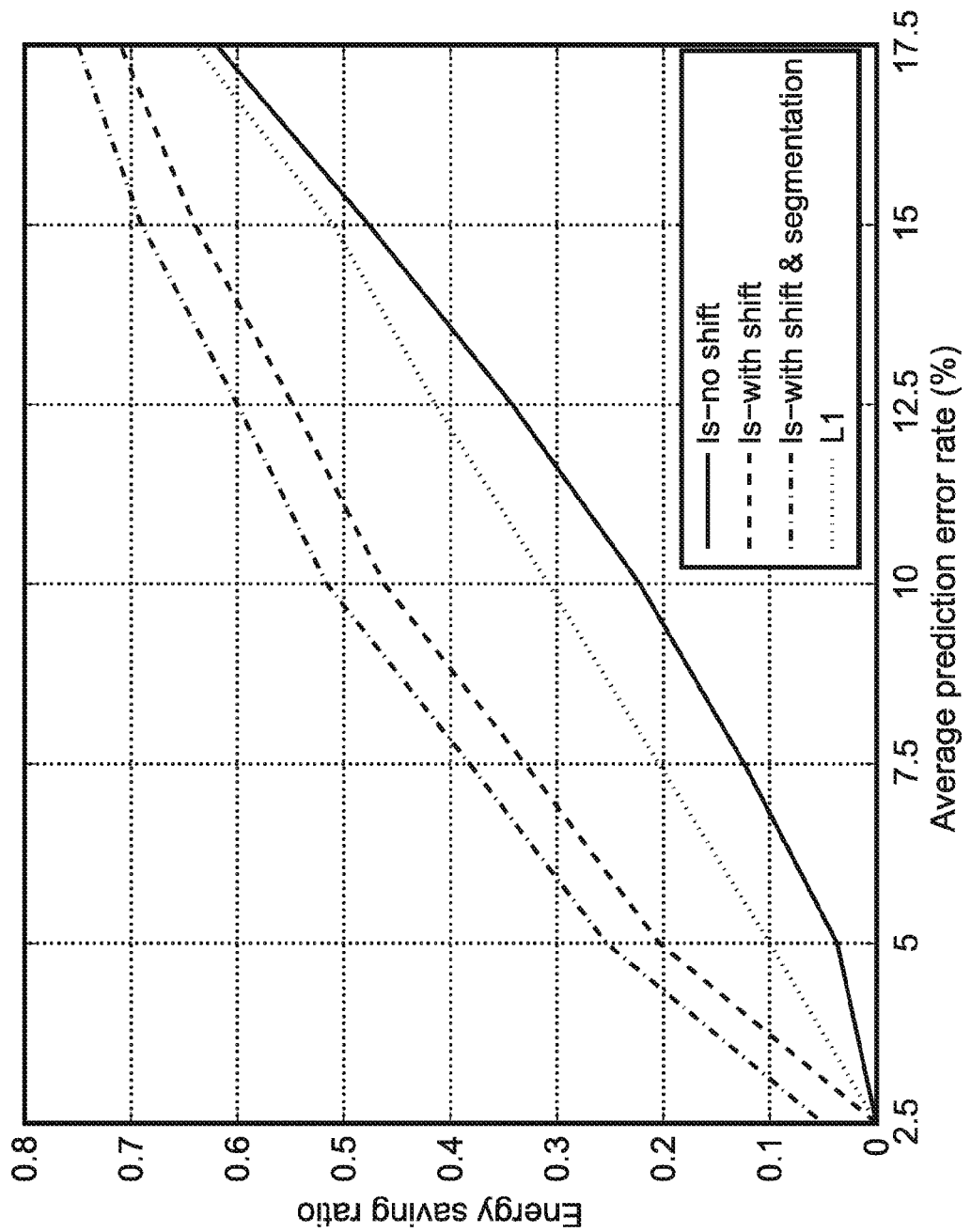

FIG. 18A and FIG. 18B show the ratio of energy savings with respect to no prediction vs. the average prediction error for the whole sensing network, for (A) the individual case and (B) the general case.

Figure 18C:
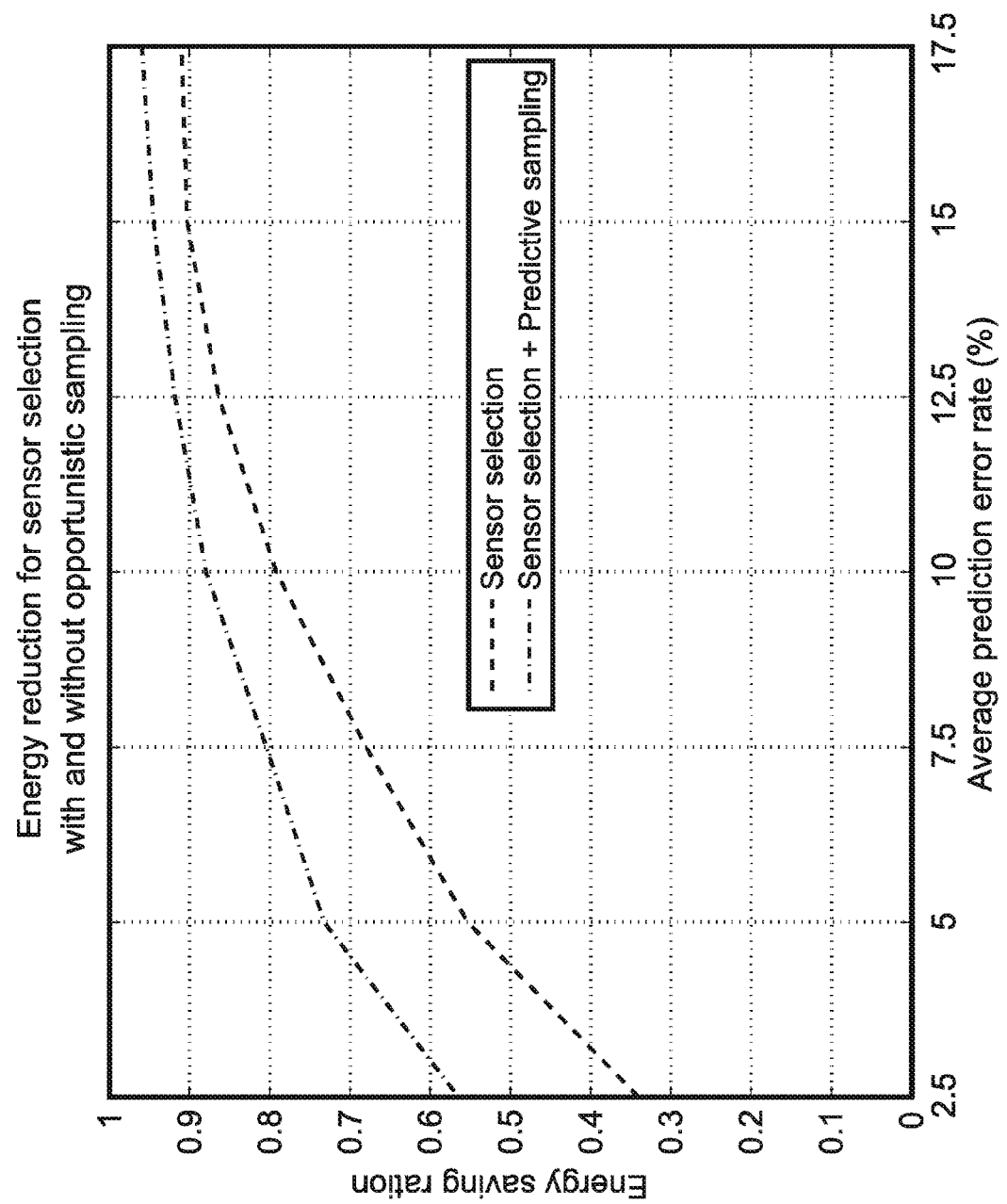

FIG. 18C shows the same relation as FIG. 18A and FIG. 18B for opportunistic sampling before and after sensor selection.

Figure 19:
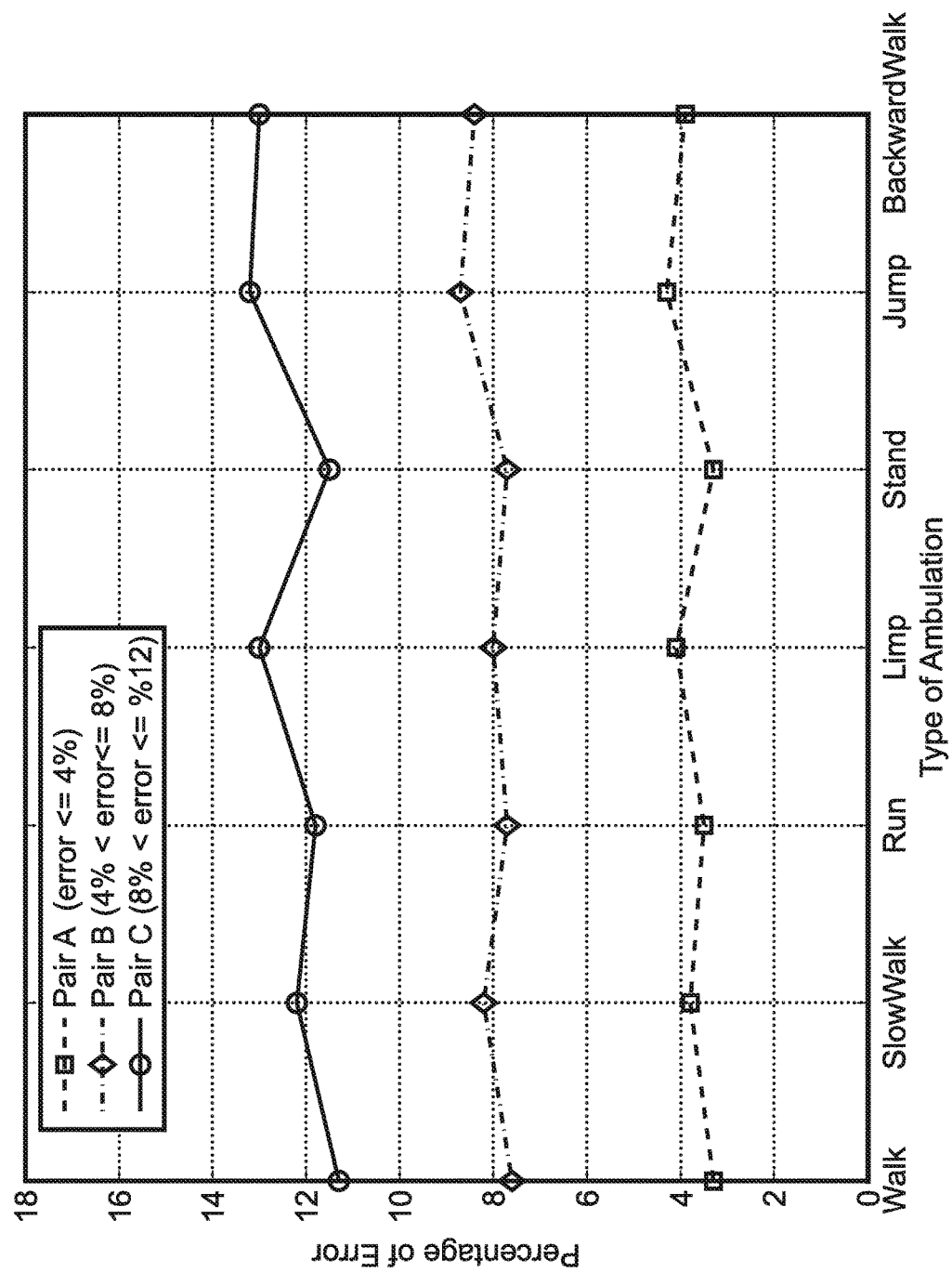

FIG. 19 shows the prediction error for each sensor pair across different types of human activity and ambulation patterns, averaged over test subjects.

Figure 20:
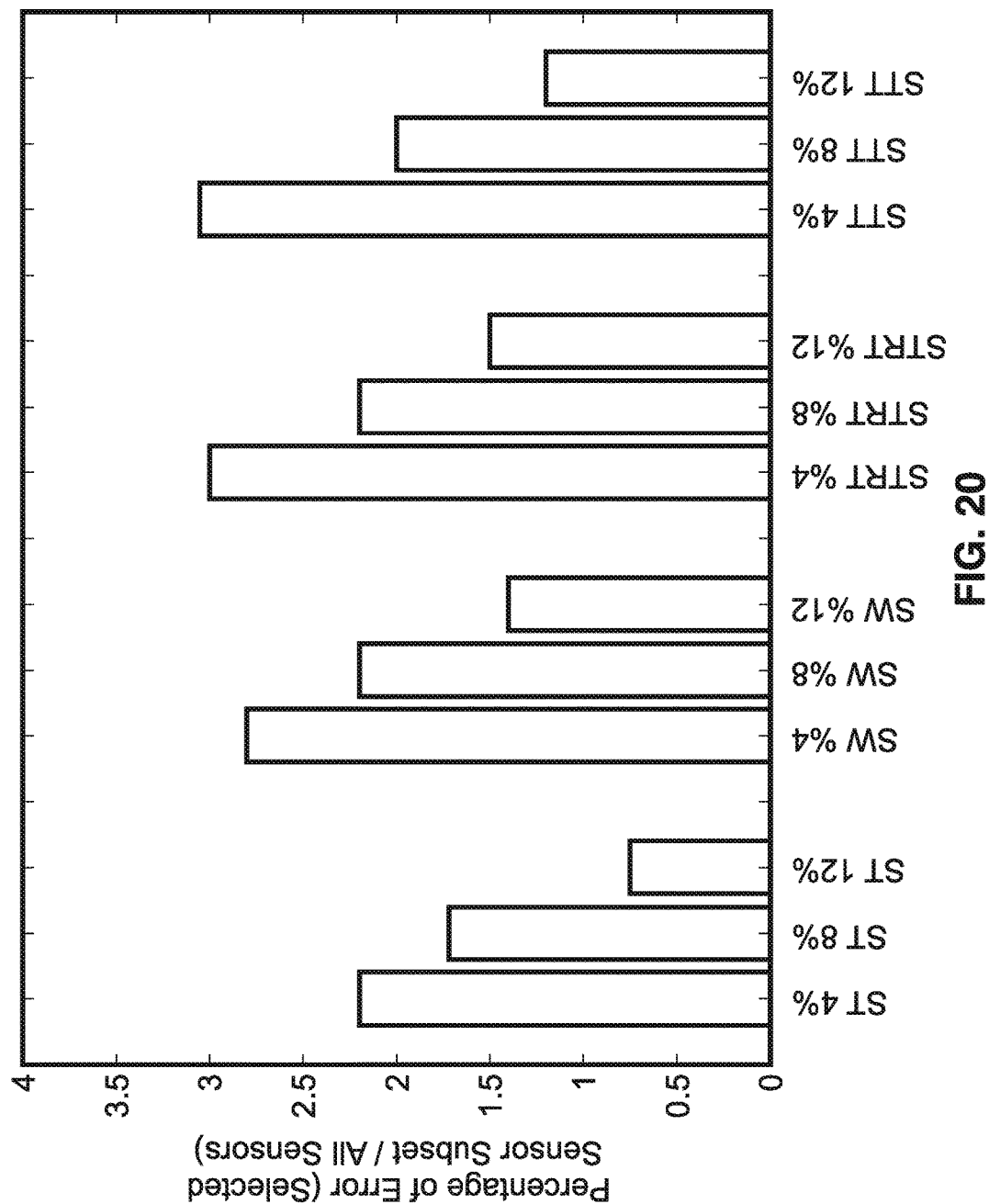

FIG. 20 shows the percentage of error introduced from calculating gait parameters using selected sensor set with bounded prediction maximum error of 4%, 8% and 12%, with respect to computed gait parameters.

Figure 21:
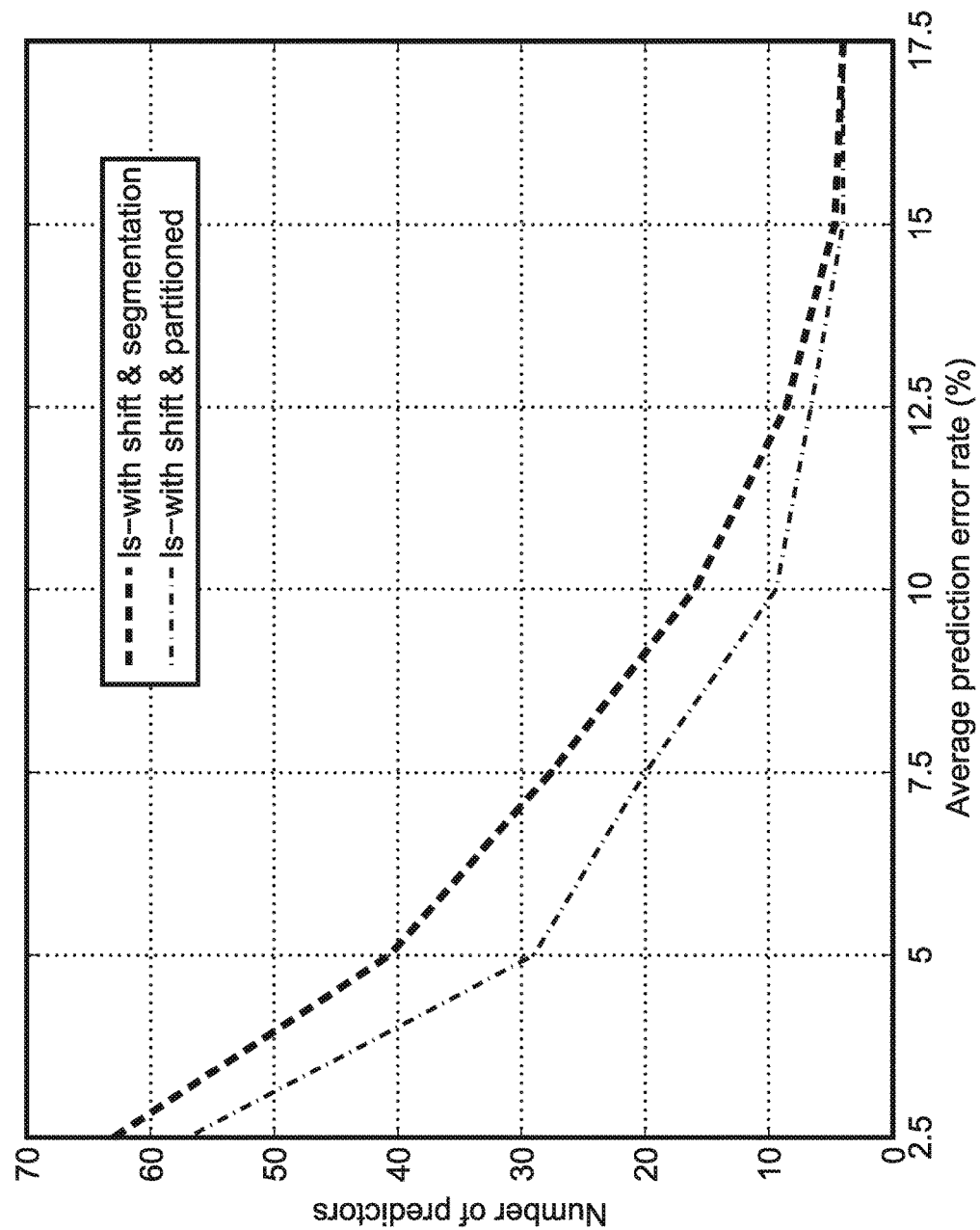

FIG. 21 shows a comparison of minimum predictors with using time-partitioned multi-predictors.

Figure 22:
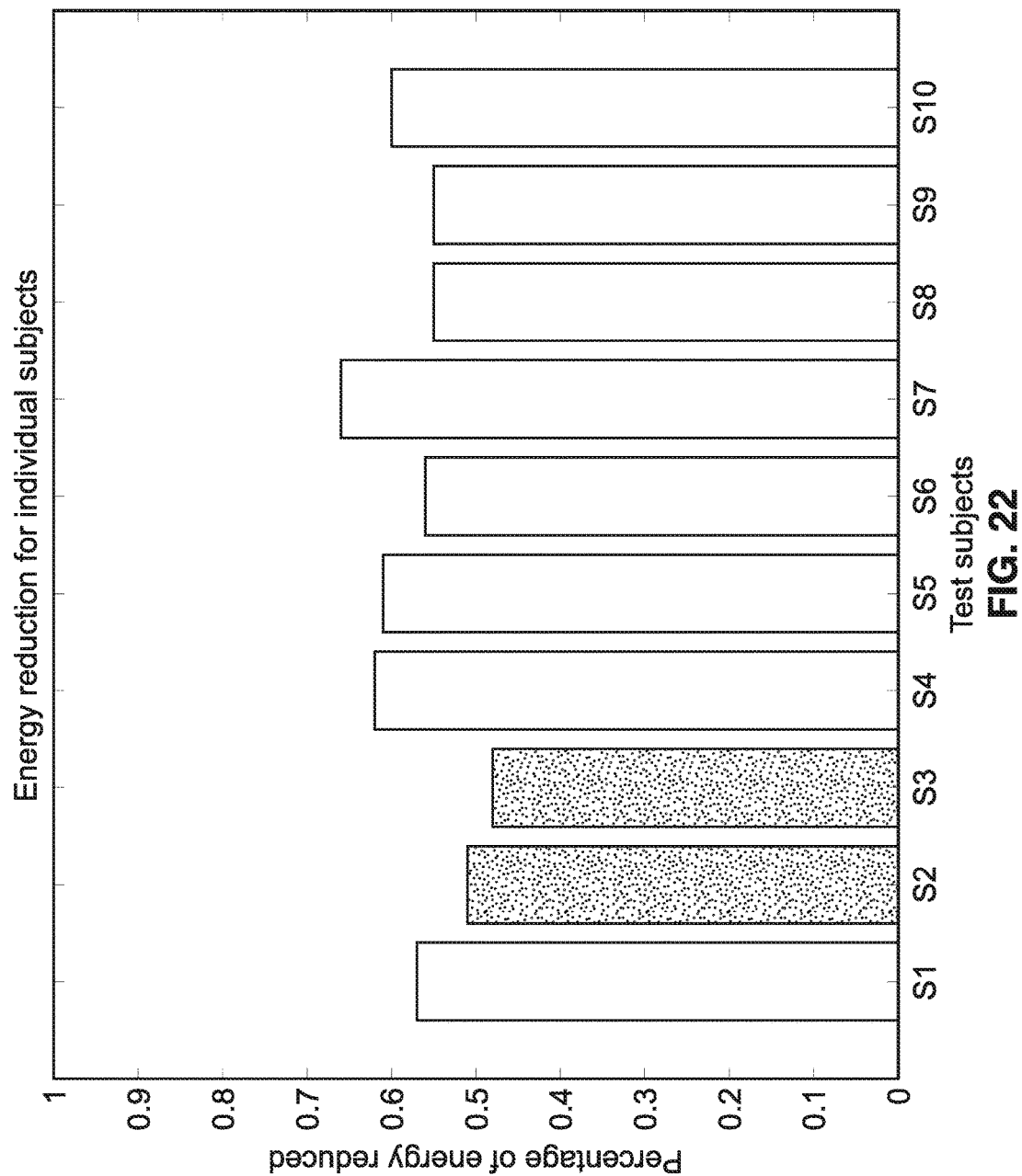

FIG. 22 illustrates the ratio of energy savings only using opportunistic sampling.

DETAILED DESCRIPTION OF THE INVENTION

1. Overview

The present invention is described below with reference to FIG. 1 through FIG. 22. The embodiments detailed below a primarily directed to a wearable sensor system and method, and particularly a system and method for sensing within a shoe. However, it is appreciated that the systems and methods presented herein may be applied to any number of physiological conditions.

Section 2 details a low-power wearable sensing system. In Section 3, signal properties of this system are describes, which are influenced by user behavior and of which we take advantage for optimization. In Section 4, the relationships between pairs of sensors are mathematically formulated, the predictor-to-base sensor model is derived, and the predictor selection objectives are defined. Section 5 details algorithms and methods for sensor selection. Section 6 details the changes in prediction error in different types of ambulation and abnormality/irregularity detection. In Section 7, opportunistic sampling methods are shown, using prior knowledge of human behavior is used for identifying reliable triggering predictor. Section 8 presents experimental results and achieved performance.

2. Low Power Sensing System Configuration and Development

Figure 1:
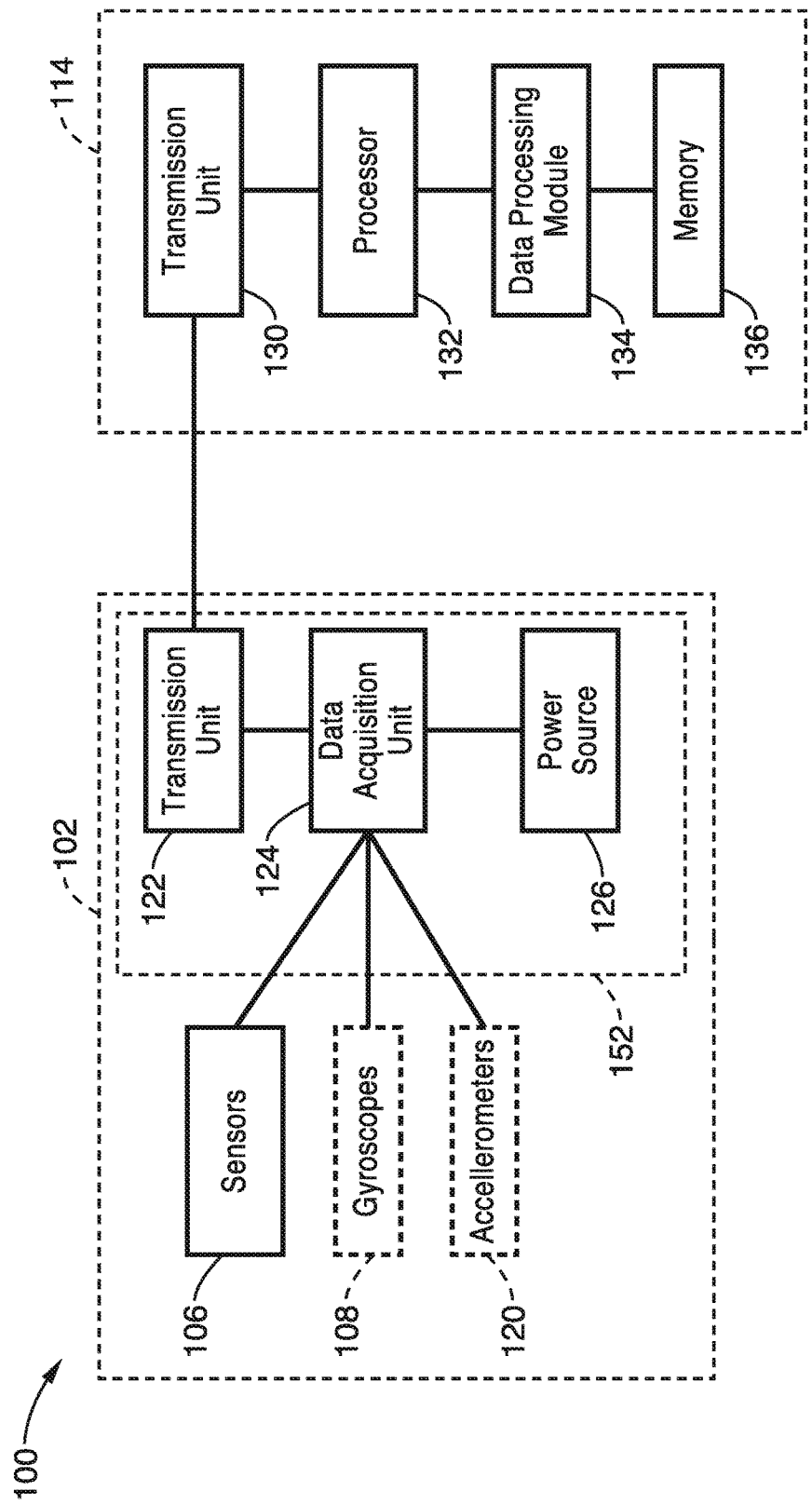
FIG. 1 illustrates a schematic diagram of a low-power consumption sensor system in accordance with the present invention.

FIG. 1 illustrates a schematic diagram of a low-power consumption sensor system 100 in accordance with the present invention. Sensing system 100 generally comprises a sensing node 102 in wireless communication with an external processing unit 114. The sensing node 102 comprises a sensor array 106 (e.g. two or more sensors, such as pressure sensors, etc.) and an electronics package 152. The electronics package generally includes a processor/data acquisition unit 124 for acquiring data from the sensors 106, a radio/transmission unit 122 for transmitting the acquired data to the external processing unit 114, and power source 126 (e.g. battery) for powering the device. It is appreciated that electronics package 152 may contain other components (e.g. Analog-digital converter, memory, USB connectors or the like) not shown.

In addition to the sensors array 106 (e.g. pressure sensors), the sensor node 102 may optionally include secondary sensors, such as gyroscopes 108 and accelerometers 120, which may be used for activity recognition, motion tracking, gaming applications, etc.

The remote processing unit 114 may comprise any device, (e.g. cell phone, watch, computer, etc.) that comprises a radio/transmission unit 130 for receiving the data signal, a processor 132 for analyzing the data according to data processing module/programming 134, and memory 136. Data processing module 134 may comprise a pre-generated sensing policy (e.g. policy for selectively acquiring data from only a subset of all sensors in array 106) learned via the methods detailed in Sections 3-7 below. Alternatively or additionally, data processing module 134 may include learning programs using one or more of the methods detailed in Sections 3-7 below, which may then later be used to establish a sensor policy for a particular physiological trait or ambulation.

Figure 2:
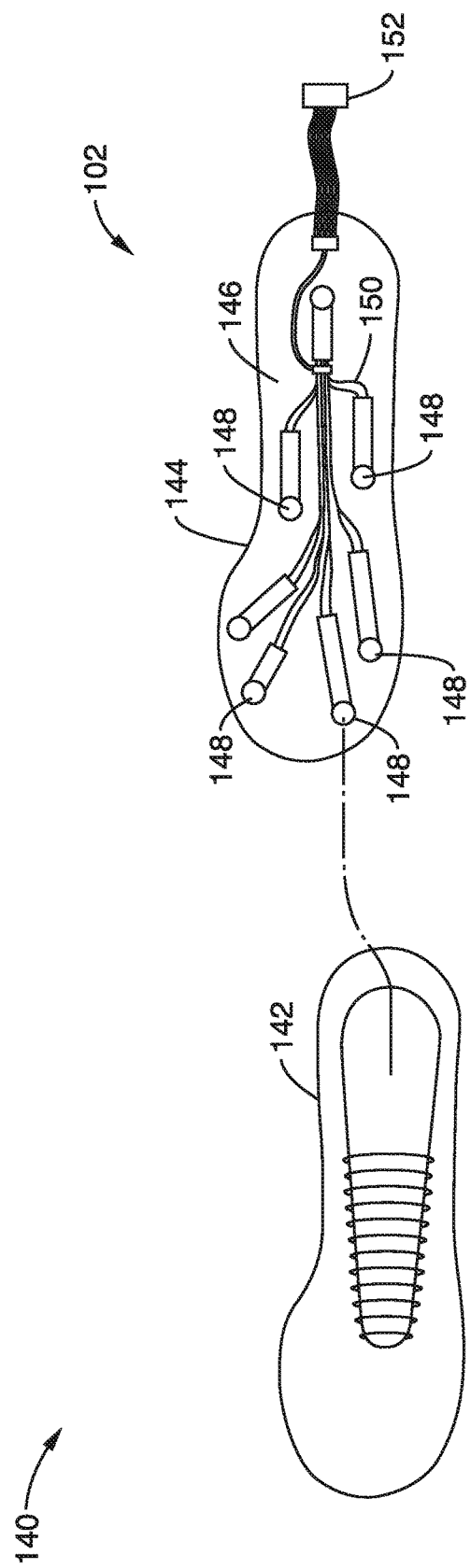
FIG. 2 illustrates a schematic diagram of a lightweight smart shoe comprising an insole that is exemplary of a potential sensor node illustrated in the system of FIG. 1.

FIG. 2 illustrates a lightweight smart shoe 140 comprising an insole 144 that is exemplary of a potential sensor node 102 of system 100. The insole 144 comprises an array of pressure sensors 148 that are coupled to an electronics package 152 (with embedded data acquisition unit and radio transmission) via leads 150.

The insole 144 may comprise a pressure sensing material 146 having passive resistive sensors 148, e.g. sensors produced by Tekscan. Alternatively, material 146 may comprise a piezoresistive fabric, e.g. produced by Eeonyx. When using passive resistive sensors, the sensors 148 may be placed under the insole 144. In the case of the piezoresistive fabric (not shown), the fabric may be cut such that it covers the entire surface under the foot, with two conductive layers (not shown) placed on both sides of the fabric. The sensing areas are the parts of the fabric covered by conductive material on both sides.

Sensor 148 placement, especially for resource-constrained systems, is preferably established using an understanding of the environment where the sensors are being deployed so that (1) decisive and important areas are covered and (2) resource usage is done intelligently, meaning one does not deploy more resources than necessary. Therefore, an understanding of the pressure distribution and behavior beneath the foot is integral to proper sensor placement, particularly for the objectives are: energy requirements, sampling accuracy, coverage, etc To better learn the signals resulting from the exertion of pressure by both feet, a plantar pressure mapping system that covers the entire surface under the foot. FIG. 3 illustrates a pressure sensor location map 162 under the foot for a Pedar insole. Pedar is a pressure distribution measuring system for monitoring local loads between the foot and the shoe. It is comprised of insoles equipped with a grid of 99 pressure sensors (shown as 1-99), which cover the entire area under the foot, and a data acquisition unit (not shown) capable of data sampling and transmission to a PC over a wireless (e.g. Bluetooth) connection. Although the Pedar map 162 can provide complete information about the plantar pressure, high data sampling and transmission rates make such a system suboptimal for low power applications such as use as sensor node 102, due to the short lifetime of the system. However, the Pedar sensor 162 may be a valuable learning tool, as described below with respect to FIG. 4.

Smart shoe 140 is capable of sensing plantar pressure, movement, direction, rotation and other physiological characteristics of the human foot. Smart shoe 140 may also be used for instability and gait analysis outside of a laboratory environment, outdoor gaming, sports, workplace safety, and environmental data collection.

In almost all of the above specified applications, long term and continuous operation is required. While, in the outdoor environment, the process of charging batteries is not a convenient or even possible task. High sampling rate, continuous data collection, and large volume data transmission have traditionally presented tremendous challenges to operating such a mobile platform.

It is appreciated that while the smart shoe 140 is a particularly beneficial application of the sensing system 100, any sensing application where a plurality of sensors are measuring a physiological characteristic may be implemented in accordance with the principles of system 100 to benefit from its inherent advantages. For example, sensor system 100 may comprise a plurality of leads for an EKG, or other heart-monitoring device, temperature sensors, etc.

In general, wireless communication is one the most power hungry units in mobile or lightweight embedded sensing systems. Table 1 summarizes the power and energy consumption of the radio and the processor of a MicroLEAP sensing node (which may be used as the main sensor node 102 responsible for sensing and transmitting the collected data from the sensors).

Therefore, in a network of N sensors, eliminating the sampling of a subset of the sensor data can drastically reduce the required energy consumption. The objective of the system 100 is not to disregard the data from sensors, but rather provide a means to retrieve the information later on. In other words (as described in further detail in Section 4), the system 100 is configured to sample only a small subset of sensors, and later, (e.g. in a base station or other processing center (see FIG. 4)) predict accurately the data values of the whole sensor network.

Figure 4:
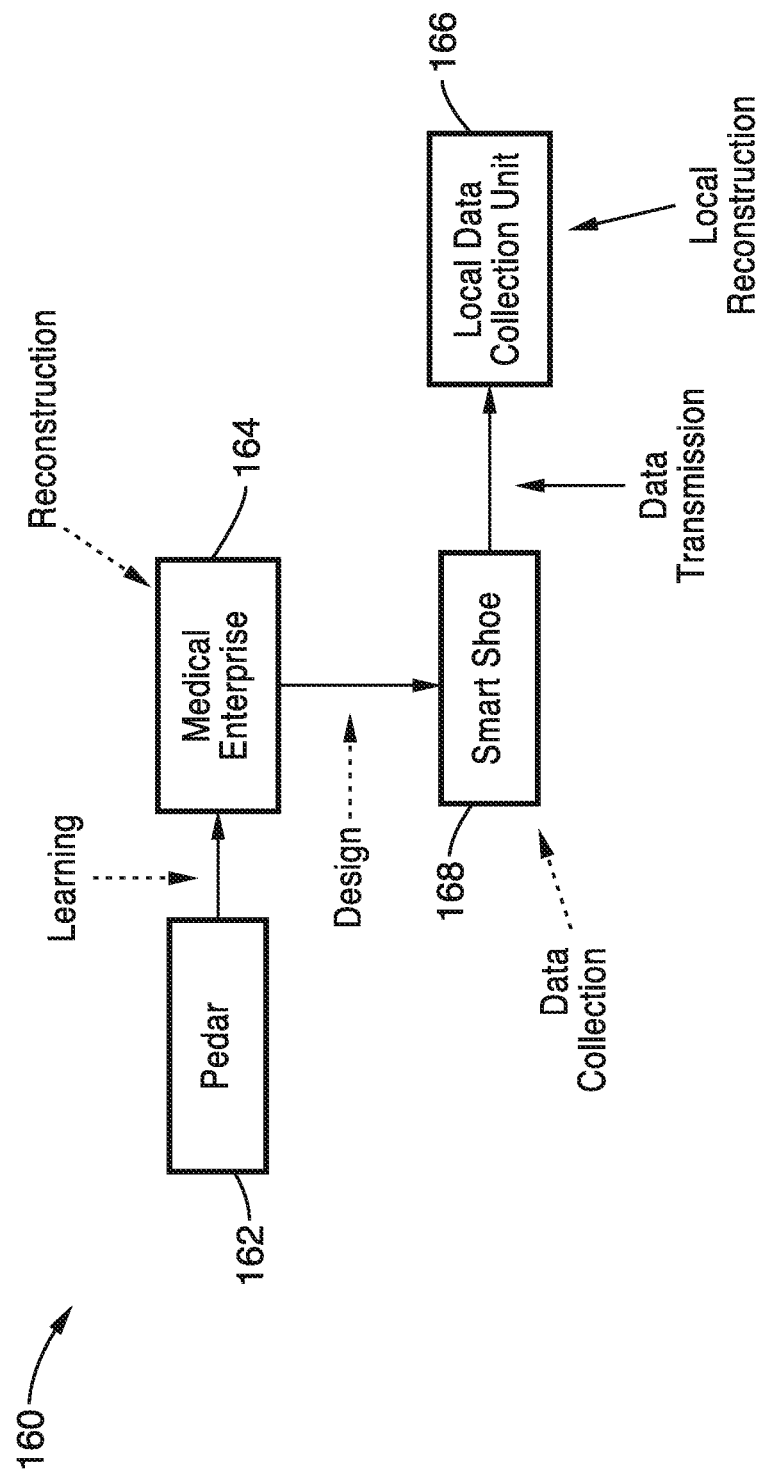
FIG. 4 illustrates a development system for generating a sensing device with a sensing policy configured to sample a subset of the sensor data to reduce energy consumption.

FIG. 4 illustrates a development system 160 for generating a sensing device 168 (e.g. smart shoe) having a sensing policy configured to sample a subset of the sensor data to reduce the required energy consumption. Learning of a physiological characteristic (e.g. plantar pressure) may be performed via a secondary sensor system (e.g. Pedar sensor 162), or via data processing software in local data collection unit 166 (which may be external processing unit 114 in FIG. 1). Data from devices 162, 166, is uploaded to a base or medical enterprise 164. In both the local collection unit 166 and medical enterprise 164, collected data may be used to reconstruct all the sensor values for learning (e.g. from data processing incorporating one or more of the methods detailed in Sections 3-8 below). The reconstructed data may then be used to design a smart sensor (e.g. lightweight/low-power smart shoe) having a sensor policy calibrated from the learned/reconstructed data (which may be within the shoe itself, or transmitted from the local collection unit 166.

Figure 5:
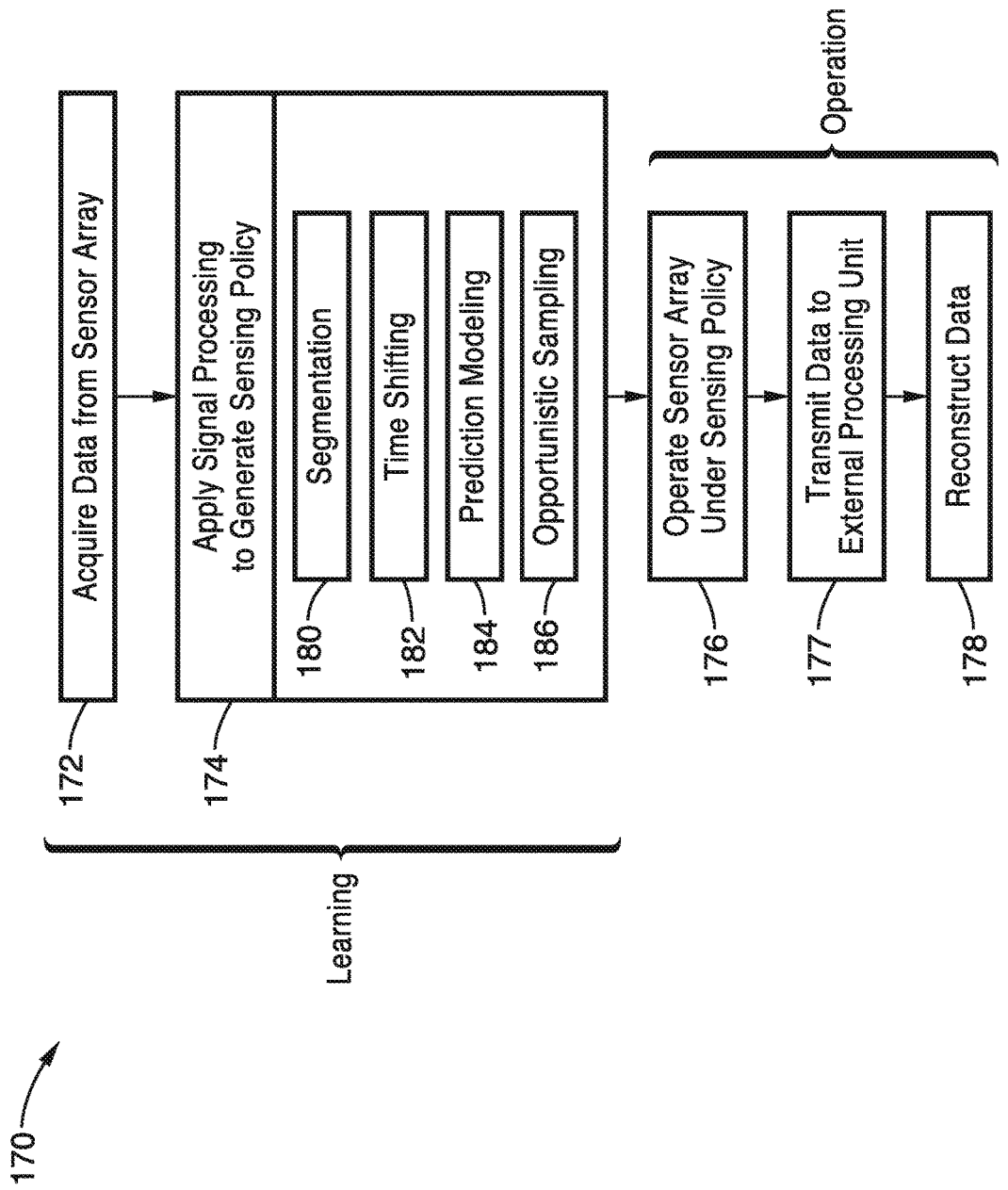
FIG. 5 shows an exemplary method for operating a sensing device according to a sensing policy of the present invention.

FIG. 5 shows an exemplary method 170 for generating and operating a sensing device according to a sensing policy. At block 172, data is acquired from a sensor array representative of the physiological characteristic to be sensed. This may be from via local sensing device 166 receiving data from sensor array 168, or from medical enterprise 164 obtaining data from a secondary sensor array (e.g. Pedar array 162).

Next, at block 174, signal processing techniques (generally characterized by the physiological behavior being sensed) are applied to the acquired data to generate the sensing policy. This may comprise one or more signal processing techniques, including segmentation 180 (detailed further below in Section 3), time shifting 182 and prediction modeling 184 (detailed further below in Sections 4-6), and opportunistic sampling 186 (detailed further below in Section 7). Blocks 172 and 174 generally comprise a learning mode involving pre-sensing processing to "train" the sensing device to become more energy efficient. Once the sensing policy is generated, it may be uploaded into memory on either the sensor node 102 or the external processing unit 114.

The sensor array (e.g. 102 in FIG. 1 or smart shoe 140 in FIG. 2) may then be operated at block 176 according to a sensor policy stored either on the sensing device 102 or the external processing unit 114. The sensing unit 102 will generally only retrieve data from a subset of sensors at given times, according to the sensing policy. This data set is transmitted to the external processing unit 114 at block 177. At block 178, the processing unit 114 then reconstructs the data to retrieve unsampled data according to the sensing policy, which may reside in data processing module 134 (see FIG. 1). It is appreciated that once a sensing policy is generated and stored in memory on the system, the system 100 need only perform operation steps 176, 177 and 178 to acquire and process sensed data.

3. Signal Properties

The extracted patterns and signal semantics, along with behavioral properties, may be used to model the relationship among sensor signals. For example, plantar pressure signal properties corresponding to human ambulation may be learned in order to identify physiological and behavioral trends.

A plantar pressure signal can be segmented based on its behavior, which is imposed by human gait characteristics. Each step a person takes may be divided into three segments: (1) airborne; (2) landing; and (3) take-off. FIG. 6 demonstrates the extracted segments in the plantar pressure signal, (A) airborne, (B) take-off and (C) landing. The airborne state A is defined as the time during which a particular foot is not touching the ground. The landing state C is defined as the time from when the signal starts increasing its amplitude from the base offset value (calibrated zero pressure) until exactly before it starts decreasing its value. The landing state C for each part of the foot, then, is the time during which the body's weight is applied to that particular sensor. Finally, the take-off state B is the time interval during which the signal's amplitude decreases from its peak to the base offset value.

Pressure signal characteristics such as morphology, amplitude, and pattern are influenced by an individual's physiology and walking behavior. For example, FIG. 8A and FIG. 8B show pressure readings from all 99 sensors recorded from a Pedar sensor array 162 for two test subjects, two steps each, where one had flat feet FIG. 8A and the other had hollow feet. The locations of sensors under the foot are based on the pressure sensor map 162 shown in FIG. 3.

As FIG. 8A and FIG. 8B suggest, the active pressure area is greater for the flat-footed person, while the amplitude difference between the active pressure and passive pressure areas for the hollow-footed person is much higher. Furthermore, the pressure patterns and signal morphology are almost the same in each step for the same test subject though different between the two. It is important to note that even though the morphological similarities might not be exactly the same for different types of ambulation, the patterns and underlying behavior, which are imposed by human locomotion characteristics, will be consistent. This is discussed in further detail below in Section 6.

The maximum amplitude of a signal is dependent on the relative position of the sensor to the person's center line of pressure progression under the feet; sensors closer to the center line of pressure will record higher pressure values compared to those that are located at the border of the active and passive pressure areas Sensors that are located on the center line of pressure or on the lines parallel to it demonstrate almost identical behavior but at different times. Therefore, the sensors can be divided in the active pressure area into sets, where data extracted from all sensors in the same set have similar morphology and almost identical shape when shifted. This implies that the signal's behavior is propagating onto different sensors in the same set. The consistent progression in data modeling and predictor selection is utilized. FIG. 7 shows two signals at their original times and when one is shifted toward the other. The top graph shows base and predictor signals at original times. The bottom graph shows base signal time-shifted toward predictor signal, where resulting signals are almost identical.

4. Prediction Modeling

In order to predict the behavior of the sensors from each other, it is instrumental to use a good prediction model to minimize prediction errors. Due to sensors' diverse locations and their behavior under the foot during human motion, it is impossible to have a single fitting model to be used as the prediction function across sensor pairs Therefore, in order to avoid cost and complexity of managing many prediction models, we take advantage of shifting signals. Due to consistent propagation of applied pressure under the active pressure sensing area, there exists a shift for a potential base sensor toward the predictor sensor's direction, which will align the two sensor values such that they will have an overlap between their landing and take-off states. Measurements show that once the base sensor is shifted toward the predictor sensor, such that there is an overlap among their landing and take off states, three different mathematical models are preferably used to present the best prediction function between any two pairs of sensors.

The first fitting model is a linear function, while the other two are isotonic. The linear model is the best predictor when two pairs of sensors have complete overlap between landing and take-off states. The other two isotonic models, which are composed of piecewise linear and quadratic models, are the best predictors when take-off and landing states of the base sensor and the predictor sensors are not completely aligned together and either or both are aligned with the other's airborne state FIG. 9A through FIG. 9C demonstrate the fitted linear curve and the isotonic curves, which illustrates the mathematical relationship between values from two different pairs of sensors, namely the predictor and the base sensor. In particular, FIG. 9A through FIG. C show the relationship between predictor vs. base sensor when: (a) the take-off and landing states are overlapping; (b) the landing or take-off state of the base is overlapping with the airborne state of the predictor; and (c) the landing or take off state of the predictor is overlapping with the airborne state of the base.

4.1 Prediction Error

Generally, there are two objectives for prediction accuracy, while fitting the data using the above specified prediction functions. The first objective is to create the model such that it minimizes the sum of the squares of the residuals or least square as described in Equation (1), which is basically the least-squared method (ls). The second objective is to minimize the sum of the absolute values of the residuals as described in Equation (2), otherwise known as the L1-model. Equations (1) and (2) are as follows:

$$\text{minimize}\left(\text{sqrt}\sum_{t=1}^{m} r(t)^2\right) \quad \text{Eq. 1}$$

$$\text{minimize}\left(\sum_{t=1}^{m} |r(t)|\right) \quad \text{Eq. 2}$$

The process of sensor predictor selection is evaluated using both of these error definitions.

4.2 Predictor Selection Objectives

The objective in this section is directed to select a potentially small sub set of deployed sensors along with prediction functions such that by only utilizing that small set of sensors, all sensing data can either be measured directly or predicted with an acceptable error bound. Let us consider two sensors $s_i$ and $s_j$ and assume the corresponding sensor values as functions of time are denoted as $g_i(t)$ and $g_j(t)$. For every pair of sensors we create a collection of predictors $\Phi_{ij} = \{\varphi_{ij1}, \ldots, \varphi_{ijm}\}$. $\varphi_{ijk}$ represents a predictor function for sensor $s_j$ that is based on shifted values from sensor $s_i$ by k samples. In other words, if the predicted value for sensor $s_j$ is denoted by $g^*_j(t)$ we have:

$$g^*_j(t) = \varphi_{ijk}(g_i(t-k)) \quad \text{Eq. 3}$$

For a given predictor there is a prediction error associated with it. We use different cost functions for prediction error as described in Section 4.1. For instance, least square based prediction error can be presented as:

$$\varepsilon(\phi_{ijk}) = \frac{\sum_{t=1}^{T}(g_j(t) - \phi_{ijk}(g_i(t-k)))^2}{g_j(t)^2} \quad \text{Eq. 4}$$

For a given sensing system, the prediction transform matrix is defined as below:

$$\Psi_{1 \times n} = \begin{pmatrix} \ddots & & \\ & \phi_{ijk} & \\ & & \ddots \end{pmatrix} \quad \text{Eq. 5}$$

where $1 \leq n$ is the number of predictors denoted by $P = \{p_1, \ldots, p_l\} \subseteq S$. Now we can define the problem. Sensor predictor selection objective can be formulated as:

$$\text{minimize}(1 = |P|) \quad \text{Eq. 6}$$

such that:

$$\forall 1 \leq j \leq n, \exists i, s.t. \Psi_{ij} \neq \emptyset \quad \text{Eq. 7}$$

$$\forall \Psi_{ij} \neq \emptyset, \epsilon(\Psi_{ij}) \leq \delta \quad \text{Eq. 8}$$

The constraint in Eq. 7 guarantees that for any given sensor, there is at least one predictor whereas the constraint in Eq. 8 enforces that maximum prediction error for any given sensor is less than the target threshold of $\delta$, where $\delta$ is an input to the problem defined by the user or is application driven.

4.3 Time-Partitioned Predictors

The previous section illustrates how a sensor can be used as a predictor of values for a secondary sensor. It is also possible to have multiple sensors in some sort of collaborative fashion predict the values of a secondary sensor. Collaborative prediction can be in the form of continuous multi sensor predictors or a time-partitioned single predictor or a combination of both.

Continuous multi sensor prediction (CMSP) is when multiple sensors are used to predict the values of a target sensor. In such a setting the prediction function can be represented in general format as:

$$g^*_j(t) = \varphi_j(g_i(t-k_i), \ldots, g_{i_{m-1}}(t-k_{i_{m-1}})) \quad \text{Eq. 9}$$

where $g_i(t-k_i)$s are the m sensors used to predict sensor j, each with the corresponding shift of $k_{i_{m-1}}$. Time-partitioned single predictor (TPSP), on the other hand, refers to the setting where at each point of time, one sensor is responsible for prediction and that sensor varies across time based on some conditions that we cover in this section. The time domain is divided into segments $\tau_i$s, and within each segment one sensor is responsible for the prediction.

To represent TPSP formally, we define a partition selector function $T_p(t,s_j) = s_i$ where t is the sample number or time stamp and $s_j$ is the sensor to be predicted. The return value of this function is $s_i$, which is the best predictor for $s_j$ for that sample.

Therefore TPSP can formally be presented as:

$$g^*_j(t) = \varphi_j(g_i(t-k_i)) \Leftrightarrow T_p(t,j) = i \quad \text{Eq. 10}$$

4.3.1 TPSP ⊆ CMSP

It is evident from the definition of CMSP that TPSP is a special case of CMSP. Basically, TPSP can be viewed as CMSP where the prediction function 9 includes the partition selector function within itself. Reasoning behind separating these two is the difference in analytical approach in finding TPSP since solving CMSP can potentially be very hard.

4.3.2 TPSP Modeling and Partitioning.

The partitioning function $T_p$ is defined based on the state of behavior of the human locomotion stages. Basically, the time for each sensor is divided into segments as defined in Section 3, where each segment corresponds to a semantically well defined stage of locomotion Therefore, the prediction accuracy/performance of sensor $s_i$ is evaluated individually for any of the time partitions. Let us assume the data from each sensor can be divided into k segments or partitions. The prediction relation across to sensors $s_i$ and $s_j$ is constructed as follows. Each sensor is represented with k sub-sensors $S_i^l$ where l=1 ... k. This representation holds for both the predictor and the sensor being predicted.

FIG. 10 illustrates and compares TPSP vs. the single prediction method. Diagram 190 represents the single prediction method, and diagram 192 shows the representation of the predictor $s_i$ in time partitioned setting. The edge labeled $e_{ij}^{ab}$ corresponds to the prediction error when segment a of sensor $s_i$ is used to predict the values of segment b in sensor $s_j$. Here, $s_i^a$ represents the sensor i data during stage/segment a; the same notation holds for predicted sensor b 4.3.3 Time-Shift Normalization.

All the prediction functions (such as Eq. 3) are time preserving in the sense that the sample count and the duration to be predicted is the same as the sample count and duration of the source data. When it comes to TPSP, in order to maintain consistent partitioning of the sensors, segmentation of all sensors should lead to the same-length intervals within each period. In other words, we need a unified segmentation of the sensor data so that the duration of a particular segment is the same across all the sensors. To better illustrate this notion, we have plotted the data for three sensors in FIG. 8A and FIG. 8B, which show raw pressure patterns from three sensors (FIG. 8A) and after time-shift normalization (FIG. 8B). Unified signal segments are illustrated for the middle period in the bottom plot In FIG. 8A and FIG. 8B, the pressure values from three sensors are normalized in time so that the three predefined pattern segments (as described in Section 3) have the same length in time. Therefore, when it comes to TPSP, dividing the sensors as shown in FIG. 8A and FIG. 8B will lead to mutually disjoint coverage of the predicted sensor, and there is a one-to-one mapping from the samples used for prediction to samples to be predicted.

5. Predictor Selection

The first step of the sensor selection process is to generate the prediction functions $\varphi_{ijk}$. Each sensor is potentially a predictor. In the context of prediction, we refer to predictor sensors as $p_i$ and the sensors being predicted are denoted as base sensors, $s_i$. For a given predictor sensor $p_i$, n×m predictor functions are generated: $\{\varphi_{ijk}\}$ where $1 \leq j \leq n$ and $1 \leq k \leq m$.

A prediction error corresponds to each predictor function represented as $\epsilon_{ijk}$ which is computed using Eq. 4. Predictor functions are generated as described in Section 4.1

Top predictor set of sensor $s_j$ is defined as:

$$T_j = \{p_{i_1}, \ldots, p_{i_k}\} \text{ s.t. } \epsilon_{pjk} \leq \delta \qquad \text{Eq. 11}$$

For each sensor which is a top predictor (i.e. $\forall p_i \in \cup T_j$) we create a set of base sensors which that predictor is among the top predictors.

In other words:

$$\pi_{p_i} = \{s_{j_1}, \ldots, s_{j_l}\}, \text{ s.t. } \forall s_j \in \pi_{p_i}, p_i \in T_{s_j} \qquad \text{Eq. 12}$$

Basically, $\pi_{p_i}$ represents the sensors which can be predicted by sensor i with prediction error less than $\delta$.

5.1 Combinatorial Iterative Component Assembly

The goal in sensor selection is to find a minimal set of predictors, $\Pi = \{p_i\}$, which can be used to predict all other sensors. Formally this objective can be stated as minimizing $|\Pi|$ such that:

$$\forall s_j, \exists p_i \in \Pi, \text{s.t.} p_i \in T_j \qquad \text{Eq. 13}$$

We call this minimal set $\Pi^*$. To solve this problem, a minimum number of $\pi_{p_i}$ s which cover the whole set of sensors is selected Algorithm 1 details a process for generating a minimum set cover using combinatorial iterative component assembly. This problem is equivalent to the minimum set cover problem which is known to be NP-Hard for general graphs. Therefore, a combinatorial iterative component assembly algorithm (see Algorithm 1 below) or CICA to find the min set cover.

---

Algorithm 1: Minimum Set Cover Using Combinatorial Iterative Component Assembly

---

1: Input: $\pi_{p_i}$ for all sensors in the system and k for top set selection threshold
2: Output: $\Pi^*$ minimum set of sensors, which can be used to predict other sensors
3: $\Gamma \leftarrow$ Sort $\pi_{p_i}$ s based on number of sensor they can predict in descending order and peak top K sets
4: Y = { }
5. Index = { }
6: WHILE no set in $\Gamma$ covers all sensors in the system}
7:   FOR each set $\gamma_i$ in $\Gamma$} DO
8:     FOR each $\pi_{p_i}$ from Input DO
9:       Combine covered sensors in $\gamma_i$ and $\pi_{p_i}$ and add the new set to Y
10:      Add predictor sensor to $\gamma_i$'s corresponding index
11:    END FOR
12:   END FOR
13:   $\Gamma \leftarrow$ Sort sets in Y based in number of sensors they cover in descending order and peak top k sets
14: END WHILE
15: $\Pi^* \leftarrow$ Index corresponding to largest set in $\Gamma$
16: return $\Pi^*$

---

CICA works in the following way. First it will sort the set of predictors based on maximum number of sensors they can cover. Then it picks top predictors from sorted list and combine each with the initial list and create new set of predictors to base sensors map. The following process continues until there is at least one single set, which covers all the sensors. Algorithm 1 summarizes the process.

Once $\Pi^*$ is created, the $\Phi$ matrix is generated and sensor selection process is completed. The in generating the elements in $\Phi$ matrix are created in the method 200 detailed in FIG. 12. First, prediction functions are created at block 202. Next the top predictors for every base sensor are found at block 204. Next, a set of base sensors top predictor by every top predictor is created at step 206. Next the minimum set cover is found at step 208. Finally, The minimum set cover is used to create the prediction matrix at step 210.

Rows of the matrix correspond to the predictors in $\pi^*$ and the entries of the matrix are $$\Phi[p_i, j] = \operatorname{argmin}(\epsilon(\Psi_{pjk})), \text{if} p_i \in T_j \qquad \text{Eq. 14}$$

$$\Phi[p_i, j] = \emptyset, \text{ otherwise} \qquad \text{Eq. 15}$$

In other words, in the column corresponding to base sensor $s_i$, we insert the best prediction function from its top predictors.

Algorithm 2 summarizes the process:

---
Algorithm 2: Minimum Predictor Selection
---
1: Create prediction functions, $\varphi_{ijk}$
2: Find top predictors $T_{s_i}$ every base sensor $s_i$
3: Using $T_j$ s, create the set of base sensors ($\pi_{p_i}$) best predictor by every top predictor $p_i$
4: Find the minimum set cover from $\pi_{p_i}$ s and add the corresponding predictors to $\Pi^*$
5: Use $\Pi^*$ to create the prediction matrix $\Phi$
---

5.2 Generalized Sensor Selection

In general, sensor networks are deployed in a particular environment to collect specific information from that environment. Any optimization of configuration methodology will be applied to that sensor network either prior to deployment or afterward. Many of the environment-dependent offline methodologies need to be repeated if a new sensor network is to be deployed in a new place. For the system of FIG. 2, the sensing environment is the human body (in particular, the feet). Therefore, for any new test subject, some training data should be collected to efficiently select the best predictors and customize the system accordingly. At the same time, it is only natural to assume that, across different people, the sensing environments have some similarities that might cause repeating predictor selection for any new test subject redundant. To overcome this problem, it is desirable to find the globally minimum top predictors across all subjects. To achieve this, the process is modified as follows. $\pi_{p_i}$ is defined to be:

$$\pi_{p_i} = \{s_{j_1 O_1}, \ldots, s_{j_1 O_r}\} \quad \text{Eq. 16}$$

where $O_k$ represents the k th subject, and r is the total number of subjects under study. Basically, base sensors are differentiated across subjects with the secondary $O_k$ index, but predictors remain the same. Therefore, the number of base sensors to be covered by min set cover is increased by a factor of the number of test subjects. The rest of the process remains the same The main question to address is: how stable are the global predictors? In other words, if the top predictors are selected based on training data from k test subjects, how will those predictors perform for the kth+1th test subject?

Experimentally it was shown that once the number of test subjects for global predictors is around 5, the corresponding predictors are in fact global and reliable for any new subject.

FIG. 13 shows the number of predictors for various numbers of test subjects and error rate bounds. This graph was generated by running, for a given number of test subjects (say k), the generalized predictor selection of all combinations of k test subjects for whom we had reported the average predictor size. It is clear from this graph, the predictor size converges very fast once the number of test subjects passes 7. This means that, once the global predictor set is calculated for a few test subjects, these predictors can be reliably used for a new subject

6. Prediction in Different Ambulation and Abnormality Detection

Health monitoring system 100, and method 170 are configured to capture and monitor specific parameters of an underlying behavior as well as to detect irregular and abnormal behavior. In the context of human gait analysis, these parameters of interest may comprise gait features such as stance, swing, stride, step time, etc. Furthermore, abnormalities in the same context are defined over these gait parameter changes and deviations. In other words, for our system 100 to be able to detect abnormalities and irregularities, gait features would be accurately measured using the predictor sensors. Therefore, although the predictors are chosen from data collected from regular behavior, it is illustrated in the experimental sections that, using predictor sensors, gait features can in fact be measured and calculated with less error rate compared to the individual sensor prediction error rate. This further proves that predictor sets can in fact be used to detect abnormal gait patterns. Furthermore, it is shown that that selected sensors based on walking behavior are also good predictors for other types of human ambulation, such as slow walking, running, jumping, standing, walking backward, etc.

7. Opportunistic Sampling

In many environments monitored by sensor networks, individual sensor data only contain useful information for subintervals of time. In these scenarios, sensors usually record constant values until an event is triggered, which alters the values recorded by a sensor. For instance, sensor networks deployed for motion detection and object tracking will collect useful data once the presence of a moving object is detected. This does not mean that the sensor values when no moving object is present are not useful; they are constant values and are known beforehand.

This is true also for the case of pressure patterns under the foot. Once the foot is above the ground, all sensor values are zero and data becomes interesting only when the foot touches the ground again. Data processing, or a sensor policy, using opportunistic sampling will turn off data sampling from a subset of sensors and turn sampling back on when we know some event is occurring (e.g. using another sensor as a trigger to start sensing one or more dormant sensors).

Referring back to the snapshot of the data from two sensors shown in FIG. 7, the non-trivial information is when the sensors are recording non-zero values. In the context of foot pressure monitoring, an event is defined to be the duration during which a sensor's value is not constant; furthermore, event triggering time is the time stamp (or sample) when the event starts, which for sensor s is denoted as $t_s^e$. This figure suggests that the two sensors shown trigger in the same order in all steps for a similar type of ambulation. In general, there can be many pairs of sensors in the network for which triggering happens in the same order.

For example, while walking, a sensor located in the heel side will get triggered before another sensor located on the toe. Let the sensor on the heel be u and the one on the toe be v. By assigning the sensor u as the base sensor, sampling of sensor v can start after sensor u is triggered. The difference between the times when these two sensors trigger is called the triggering distance, $td = t_u^e - t_v^e$. If td=K, then instead of sampling v all the time, the sensor policy would turn off sampling of v and re-start it K samples after u is triggered. This approach has two energy-related benefits: 1) reducing sampling energy and 2) reducing transmission energy for sensors like v whose activation can be predicted.

7.1 Reliable Triggering Predictors

Sensor u can be a triggering predictor of sensor v if $td_{uv}$ can be determined with high degrees of certainty. Thus, across different time frames, the triggering distance between u and v, $td_{uv}$ may be calculated so that no information is lost with predictive sampling. Generally, $td_{uv}$ will vary if an object changes its speed of walking or performs other ambulations (e.g. running jumping, etc). Assume the period of the current pressure waveform is T. Then, the normalized triggering distance ntd is defined to be td/T. Triggering prediction reliability, or TPR, is defined as a measure of how well a sensor can predict the triggering of another sensor:

$$TPR_{uv} = \sigma^2(ntd) \qquad \text{Eq. 17}$$

which is basically the standard deviation of normalized $td_{uv}$ across a set of periodic activities. Thus, if $TPR_{uv}$ is small, using the current signal period, u can calculate $td_{uv}$ reliably. Accordingly, the triggering prediction relation is defined as $$f(u,v) = \kappa, TPR_{uv} \leq \delta \qquad \text{Eq. 18}$$

$$f(u,v) = \text{null}, TPR_{uv} > \delta \qquad \text{Eq. 19}$$

where f(u,v) is the normalized triggering distance between u and v when TPR is smaller than a given threshold κ and is not defined (i.e. u cannot reliably predict the triggering of v) when TPR is not small enough.

Next, the value of κ is determined. As shown in previous sections, the value collected by a sensor, u, is represented by $g_u(t)$, where t is the sample number or the time stamp. It is assumed that sensor v is being sampled using triggering prediction of u.

At the base station (e.g. medical enterprise 164 of local data collection unit 166 shown in FIG. 4), the data processing module may be configured to regenerate values for v, $g^*_v(t)$, to be:

$$g^*_v(t) = g_v(t); \text{sampling-on} \qquad \text{Eq. 20}$$

$$g^*_v(t) = 0; \text{sampling-off} \qquad \text{Eq. 21}$$

Sampling-on and sampling-off intervals are determined by the triggering prediction of u. The error rate for v's values will be $$err_v = \frac{\Sigma(g^*_v(t) - g^*_v(t))^2}{g^*_v(t)^2} \qquad \text{Eq. 22}$$

This error rate solely depends on how well u could have predicted v, which is a function of $ntd_{uv}$ and its discrepancy across periods. This error was experimentally calculated for different sensor pairs and established a baseline of reliable κ.

FIG. 14 illustrates precedence and triggering for two sensors (A and B). The relationship between two signals determines the order of sampling in adaptive sampling.

FIG. 15 shows the linear relationship of triggering distance to step time. Relationship between step time and the median time difference between the As shown in FIG. 15 triggering times of sensor 9, located on the heel, and sensor 86, located on the toe (see Pedar map 162 in FIG. 3). This picture enables use of the linearly to normalize the triggering distance when the step time varies.

7.2 Triggering Predictor Selection Objective

The triggering prediction method allows for better utilization of resources if the idle period of sensor v compared to the active period is large enough. In other words, if v is mostly active, there is no benefit to dynamically turning sampling on and off. A measure of the active length of a sensor is defined as $\alpha_s$, which is, for a given period T, equal to the ratio of the active interval to T.

The objective of predictive sampling is to select a subset of sensors (called trigger predictors or TP) which will be monitored all the time and can be used to determine when to start sampling other sensors; this set can yield a minimum sampling across all sensors.

Thus, if the sensor set is denoted as $S = s_1, \ldots s_n$, a feasible set of trigger predictors can be defined as:

$$TP_S \subset S, st \cdot \forall s \in S, \exists q \in TP_S : f(q,s) = \kappa \neq \text{null} \qquad \text{Eq. 23}$$

The objective becomes to find $TP^*_S$ such that:

$$\sum_{s \in TP^*_S} |g_s(t)| + \sum_{s \in S - TP^*_S} |g_s(t)| \times \alpha_S \qquad \text{Eq. 24}$$

is minimized, where:

$$\sum_{s \in S - TP^*_S} |g_s(t)| = \sum_{s \in S - TP^*_S} \alpha_S \times I \qquad \text{Eq. 25}$$

where I is the time interval under study.

7.3 TP Selection Algorithm

Every sensor can potentially have multiple trigger predictors and itself can predict the triggering of other sensors. In order to find the minimum number of predictors to minimize sampling (and therefore transmission) energy, a triggering graph $G_T = (V,E)$ is constructed as follows. Each node in this graph represents a sensor in the system, $V = \{s_1 \ldots s_N\}$. If sensor $s_i$ can be used as a triggering predictor of $s_j$, i.e. f $(s_i, s_j) = \kappa$ (Eq. 18), there will be a direct edge $e_{ij}$ in E. In other words $E = \{e_{ij} | f(s_i, s_j) = \kappa < 0\}$. Note that since triggering relations is determined per period and the triggering point is the start of the active segment of the pressure pattern, $G_T$ is a directed acyclic graph.

The problem of finding the best TP using a similar technique to the one described in Section 5.1. In other words, this problem is by nature similar to the weighted predictor selection covered in Section 5 with a different definition of predictor sets and the cost function for each set. The predictor sets are defined in Eq. 11

$$\pi_{p_i} = \{s_{j_1}, \ldots, s_{j_l}\}, s.t. \forall s_j \in \pi_{p_i} f(p_i, s_j) \neq \text{null} \qquad \text{Eq. 26}$$

The expression $f(p_i, s_j) \neq \text{null}$ basically indicates that $p_i$ can reliably predict the triggering of sensor $s_j$. The same CICA algorithm (Algorithm 1) may then be run to find the minimal set of triggering predictors, or TP*.

Furthermore, only minimizing the number of predictors does not optimize the objective. The active segments of sensors have different length. Therefore, it is ideal to select triggering predictors that have a larger active range, i.e., sample other non-predictor sensors that have the shortest length.

FIG. 16A and FIG. 16B illustrate an example of a triggering graph for a set of five sensors and two possible selection scenarios. Assume that $\alpha_v > \alpha_w$, therefore, the prediction selection in FIG. 16A will lead to a better saving by the amount of $(\alpha_v - \alpha_w) \times I$ per interval I In CICA, the comparison across sets is based on the size of the set. Here, a weight is assigned to each $\pi_{p_i}$ $$w(\pi_{pi}) = \frac{\sum_{s_j \in \pi_{pi}} \alpha_{s_j}}{|\pi_{pi}|} \qquad \text{Eq. 27}$$

The CICA algorithm is modified such that the sorting of sets is done based on the weight function above. Weighted CICA is described below in Algorithm 3.

---
Algorithm 3: Weighted Minimum Set Cover Using Combinatorial
Iterative Component Assembly
---

1: Input: $\pi_{p_i}$ for all sensors in the system and k for top set selection threshold and $\alpha_s$ for all the sensors
2: Output: $\Pi^*$ minimum set of sensors, which can be used to predict triggering of other sensors
3: $\Gamma \leftarrow$ Sort $\pi_{p_i}$ s based on $w(\pi_{p_i})$ in ascending order and peak top K sets (lowest weights)
4: Y = { }
5: Index = { }
6: WHILE no set in $\Gamma$ covers all sensors in the system DO
7:   FOR each set $\gamma_i$ in $\Gamma$ DO
8:     FOR each $\pi_{p_i}$ from Input for each _pi from Input DO
9:       Combine covered sensors in $\gamma_i$ and $\pi_{p_i}$ and add the new set to Y
10:       Add predictor sensor to $\gamma_i$'s corresponding index
11:     end FOR
12:   end for
13:   Recalculate $w(\gamma_i)$ in Y
14:   $\Gamma \leftarrow$ Sort sets in Y based on $w(\pi_{p_i})$ in ascending order and peak top k sets
15: END WHILE
16: $\Pi^* \leftarrow$ Index corresponding to largest set in $\Gamma$
17: return $\Pi^*$

8. Experimental Results

In order to illustrate the effectiveness of the above systems and methods, a Pedar sensor array 162 was used to collect sensor data across 10 individual subjects. Efforts were made to keep the subject set as diverse as possible in terms of walking behavior and sensor data variability. The subject set was composed of 7 men and 3 women, where one man and one woman were flat-footed and 2 men were overweight. Foot sizes ranged from 7 to 11.

For the collected data set, minimum predictor selection was performed with three different configurations: 1) least-square method for predictor function generation without any shift in base-sensor data (ls-noShift); 2) least-square method for predictor function generation with shift in base sensor value (ls-wShift); 3) segmentation based predictor function generation using least-square method (ls-segmentation); and 4) L1-method for predictor function generation (L1).

Furthermore, the above scenarios were repeated for the global case where the process was implemented on the aggregated data from all individuals (as described in Section 5.2). 30% of each test subject's data was used to find the best predictor, and the remaining 70% was used to evaluate the accuracy of the prediction functions. The sensor selection process was ran for a range of maximum prediction errors ($\delta$ in Eq. 8). The maximum prediction error rate ranges from 2.5% to 20%. Afterwards, simulated the estimated total energy savings was simulated on the sensor node 102 (MicroLEAP) when the minimal predictors were used to sample the data. As seen in the system architecture, one sensor node is responsible for sampling and transmission of the data from sensors.

Table 2 summarizes the performance of the proposed combinatorial iterative component assembly algorithm to find the minimum set cover versus the greedy approach. As Table 2 suggests, our the CICA algorithm outperforms the well known greedy algorithm in both the individual and general case. In the individual case, CICA outperforms the greedy algorithm by an average of 22.3% for error rates between 2.5% and 12.5%, while for 15% and 17.5% errors, the outcome is almost the same for both algorithms. In the general case, CICA outperforms the greedy algorithm by an average of 23.8% for error rates greater then 5%, while for 2.5% the outcome of both algorithms are the same FIG. 17A and FIG. 17B show the number of predictor sensors vs. the average prediction error for the whole sensing network for (A) the general case and (B) averaged over individual test subjects. FIG. 17B illustrates the number of sensors required to predict the whole sensor network data (out of 99 sensors total) versus the maximum prediction error for the four different scenarios described above. These graphs are averaged over the 10 test subjects.

FIG. 18A through FIG. 18C show the ratio of energy savings with respect to no prediction vs. the average prediction error for the whole sensing network, for (FIG. 18A) the individual case and (FIG. 18B) the general case. FIG. 18C shows the same relation for opportunistic sampling before and after sensor selection.

FIG. 18A summarizes the average power savings ratio for different maximum prediction errors. These graphs illustrate that power saving ranges from 18% to 91%, depending on the approach taken, while the maximum prediction error rate ranges from 2.5% to 20%.

Finally, the same set of experiments and simulations were repeated for the general case. FIG. 17A and FIG. 18B summarize the results. As expected, the general case tries to find a global predictor whose size is usually larger than the predictor set of an individual, and therefore energy saving ranges from 0% to 76%. Note that for a maximum prediction error rate of 2.5%, we must practically select all the sensors, resulting in no energy savings.

8.1 Time-Partitioned Prediction

The previous sections illustrated the effectiveness of various predictor selection and as expected Is-with shift and segmentation led to best sensor reduction and therefore energy savings. Furthermore, time partitioned single prediction (TPSP) was applied as described in Section 4.3.2. In order to keep the graphs readable, we excluded the results of TPSP from FIG. 17B. FIG. 21, on the other hand, compares the number of predictor sensors for TPSP vs. the best predictor selection in FIG. 17B which Is-with segmentation and shift. For low error rate thresholds, TPSP can further reduce the number of predictors by 5% to 10% but as the error rate threshold is loosened, or in other words increased, these two approaches lead to very close predictor counts. The main cause supporting this convergence is the fact that for high error rate thresholds, there are few sensors that can collectively predict the network

8.2 Prediction Among Ambulations and Abnormality Detection

The prediction error was computed in several types of human ambulation, excluded regular walk, such as slow walking, running, jumping, standing, limping, and walking backward. Three sensor pairs, were picked, where each pair consists of one base sensor and one predictor sensor. In the first pair the predictor sensor predicts the base sensor with error less then 4%. In the second set the base sensor is predicted with error of 4% to 8% and in the last set the base sensor reconstruction error is 4% to 8%. FIG. 19 shows the prediction error for each sensor pair across different types of human activity and ambulation patterns, averaged over test subjects. As the figure suggests, the prediction error only changes up to 2% across different ambulations.

As mentioned previously, the gait parameters need to be measured in order to detect irregularities and abnormalities. By using the selected sensor set it was shown that it is still possible to compute the gait parameters accurately. To demonstrate this, the following simulation was performed. First, taking all sensors into consideration, for each user during different ambulations, the gait parameters were computed. Then, the same parameters were computed by taking the produced values of selected sensors, based on the proposed algorithm, and reconstructing all base sensors.

FIG. 20 shows the percentage of error introduced from calculating gait parameters using selected sensor set with bounded prediction maximum error of 4%, 8% and 12%, with respect to computed gait parameters using all sensors while performing the following types of ambulation: slow walk, run, limp, and backward walk. This illustrates the fact that gait feature measurement error using predictor sensors is very small compared against extracting the same features using all the pressure sensors. This is likely due to the fact that a majority of the gait features capture events which are less sensitive to deviation of a single pressure point.

Therefore, as long as there is a bounded prediction error rate for the predictor sensors, this small set of sensors can be utilized to accurately capture gait abnormalities since abnormalities are functions of gait features rather than individual sensor values 8.3 Opportunistic Sampling Data Reduction The effect of opportunistic sampling was evaluated in two different setups. First, for each individual subject in our experiments, the energy reduction resulting from opportunistic sampling was measured. The energy reduction was calculated in a fashion similar to the previous section: the data volume reduction caused by sampling cuts was calculated and incorporated that into the energy consumption of the system FIG. 22 illustrates the energy savings across different test subjects. Note that opportunistic sampling by itself can reduce energy consumption from 48% to 66% depending on the individual and his/her motion patterns Next, opportunistic sampling was applied on top of predictor selection. First, the best predictors were found with the minimum least square error bounded by a range of values for each individual test subject. Then, for each subject, opportunistic sampling was applied on the predictor set (since that set is the only active set of sensors) and the data transmission rate reduction was calculated for the hybrid of these two methods. From there, the average energy reduction was estimated for each bound on error rate. FIG. 18C shows that opportunistic sampling can further reduce energy consumption from 4% to 21%, resulting in total energy reduction of 56% to 96% depending on the upper bound on error rate The data volume management systems and methods of the present invention, through the introduction of multiple stages of signal analysis and optimization algorithms, were shown to have significant implications on energy consumption and system lifetime in embedded and wearable sensing systems. Physiological signal patterns are used to develop novel prediction algorithms at different levels of information flow in such systems. The systems and methods of the present invention make expensive wearable sensing systems more feasible for everyday use, by minimizing sampling sources while enabling reconstruction of the data from all sensors. A subset of sensors were used to accurately generate the data from all sensors. In other words, the design flow adapts to the context of the sensing environment and leads to a efficient data management configuration. Signal shifting, which enables better prediction of sensor data, and data segmentation were used to further enable piecewise predictions. In addition to these prediction strategies, opportunistic sampling was used, wherein even smaller subset of sensors are selected to predict when to sample the rest of target sensors. To solve the above problems, an efficient approximation algorithm called combinatorial iterative component assembly (CICA) was developed to select best predictors for each scenario.

Embodiments of the present invention are described with reference to flowchart illustrations of methods and systems according to embodiments of the invention. These methods and systems can also be implemented as computer program products. In this regard, each block or step of a flowchart, and combinations of blocks (and/or steps) in a flowchart, can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts support combinations of means for performing the specified functions, combinations of steps for performing the specified functions, and computer program instructions, such as embodied in computer-readable program code logic means, for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s).

From the discussion above it will be appreciated that the invention can be embodied in various ways, including but not limited to the following:

In one aspect, a sensor system for sensing at least one physiological characteristic is provided, the sensor system comprising: an array comprising first and second sensors; a processor coupled to the array; said processor configured to acquire data from said first and second sensors; a transmission unit coupled to the processor; an external processing unit; said external processing unit configured to receive the acquired data via the transmission unit; and programming executable on said processor configured for carrying out steps comprising: acquiring a data subset of potential data from said first or second sensor according to a sensor policy; said sensor policy being established according to said physiological characteristic; transmitting said data subset to the external processing unit; and reconstructing said data subset to retrieve not captured from said first and second sensors.

In some embodiments, the programming is further configured to segment the signal for mutual sensor prediction of data from the first and second sensors.

In some embodiments, acquiring a data subset comprises acquiring data from only one of the first and second sensors for a given time period.

In some embodiments, reconstructing said data subset comprises predicting a data value from the second sensor based on data retrieved from the first sensor.

In some embodiments, the system further comprises: third and fourth sensors in said array: wherein reconstructing said data subset comprises predicting data values from the third and fourth sensors based on data retrieved from the first sensor and second sensors.

In some embodiments, the programming is further configured for carrying out steps comprising: placing the second sensor a sleep mode while data is being acquired from the first sensor; and wherein data acquisition is triggered in the second sensor upon sensing an event from the first sensor.

In some embodiments, acquiring a data subset comprises time-shifting data from the first sensor to at least partially overlap with said second sensor.

In some embodiments, the system further comprises: performing a binary search of the data to calculate said time-shifting.

In some embodiments, the system further comprises generating a minimum set of predictors using combinatorial iterative component assembly.

In some embodiments, the system further comprises generating a prediction matrix based on said minimum set of predictors.

In some embodiments, the programming is further configured for carrying out steps comprising: placing the second sensor a sleep mode while data is being acquired from the first sensor; wherein data acquisition is triggered in the second sensor upon sensing an event from the first sensor.

In some embodiments, the sensor array comprises a sensing pad disposed within a sole of a shoe, said physiological characteristic comprising a gait characteristic; and wherein the signal is segmented according to said gain characteristics.

In some embodiments, the signal comprises a plantar pressure signal; wherein the signal is segmented into an airborne segment, a landing segment, and a take-off segment; and wherein one or more of the first and second sensors are placed in a sleep mode during at least a portion of the airborne segment.

In another aspect, a sensor apparatus for sensing at least one physiological characteristic is provided; comprising: an array comprising first and second sensors; a processor coupled to the array; said processor configured to acquire data from said first and second sensors; a transmission unit coupled to the processor; said transmission unit configured for transmitting acquired data to an external processing unit; and programming executable on said processor configured for carrying out steps comprising: acquiring a data subset of potential data from said first or second sensor according to a sensor policy; said sensor policy being established according to said physiological characteristic; and transmitting said data subset to the external processing unit.

In some embodiments, the programming is further configured to segment the signal segmented for mutual sensor prediction of data from the first and second sensors.

In some embodiments, acquiring a data subset comprises acquiring data from only one of the first and second sensors for a given time period.

In some embodiments, the programming is further configured for carrying out steps comprising: placing the second sensor a sleep mode while data is being acquired from the first sensor; wherein data acquisition is triggered in the second sensor upon sensing an event from the first sensor.

In some embodiments, acquiring a data subset comprises time-shifting data from the first sensor to at least partially overlap with said second sensor.

In some embodiments, the sensor array comprises a sensing pad disposed within a sole of a shoe, said physiological characteristic comprising a gait characteristic; and wherein the signal is segmented according to said gain characteristics.

In some embodiments, the signal comprises a plantar pressure signal; wherein the signal is segmented into an airborne segment, a landing segment, and a take-off segment; and wherein one or more of the first and second sensors are placed in a sleep mode during at least a portion of the airborne segment.

In another aspect, a system for generating a sensor policy for a sensor array is provided; comprising: an array comprising first and second sensors; a processor coupled to the array; said processor configured to acquire data from said first and second sensors; a transmission unit coupled to the processor; an external processing unit; said external processing unit configured to receive the acquired data via the transmission unit; and programming executable on said processor configured for carrying out steps comprising: acquiring a data from said first and second sensor while measuring a physiological characteristic; performing signal processing to said acquired data as a function of said physiological characteristic; transmitting said data subset to the external processing unit; and establishing a sensor policy according to said physiological characteristic; wherein the sensor policy comprises instructions to acquire a data subset of potential data from said first or second sensor according to said physiological characteristic.

In some embodiments, the sensor policy comprises instructions to segment the signal for mutual sensor prediction of data from the first and second sensors.

In some embodiments, the sensor policy comprises instructions to acquire data from only one of the first and second sensors for a given time period.

In some embodiments, the sensor policy comprises instructions to reconstruct said data subset by predicting a data value from the second sensor based on data retrieved from the first sensor.

In some embodiments, the sensor policy comprises instructions to place the second sensor a sleep mode while data is being acquired from the first sensor; and wherein data acquisition is triggered in the second sensor upon sensing an event from the first sensor.

In some embodiments, the sensor policy comprises instructions to time-shift data from the first sensor to at least partially overlap with said second sensor.

In some embodiments, the sensor policy comprises instructions to place the second sensor a sleep mode while data is being acquired from the first sensor; and wherein data acquisition is triggered in the second sensor upon sensing an event from the first sensor.

Although the description above contains many details, these should not be construed as limiting the scope of the invention but as merely providing illustrations of some of the presently preferred embodiments of this invention.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

MicroLEAP Energy Consumption

|  | Power (mW) | Data Rate (kbps) | Energy/Bit (nJ/bit) |
|---|---|---|---|
| Processor | 2.7 | NA | NA |
| Radio | 57.5 | 250 | 230 |

TABLE 2

Minimum Selected Sensors Using CICA vs. Greedy Algorithm

| Individual | | | General | | |
|---|---|---|---|---|---|
| Error | CICA | Greedy | Error | CICA | Greedy |
| 2.5 | 63 | 78 | 2.5 | 94 | 94 |
| 5 | 41 | 52 | 5 | 65 | 82 |
| 7.5 | 21 | 27 | 7.5 | 59 | 75 |
| 10 | 14 | 18 | 10 | 42 | 58 |
| 12.5 | 11 | 15 | 12.5 | 42 | 56 |
| 15 | 5 | 6 | 15 | 24 | 32 |
| 17.5 | 4 | 4 | 17.5 | 21 | 27 |

What is claimed is:

1. A sensor apparatus, comprising:
an array comprising first and second sensors;
a processor coupled to the array;
said processor configured to acquire data from said first and second sensors;
a transmission unit coupled to the processor;
said transmission unit configured for transmitting acquired data to an external processing unit; and
programming executable on said processor, the programming configured for directing the processor to:
selectively turn off data acquisition from said second sensor according to a sensor policy related to a physiological characteristic while data acquisition from said first sensor remains turned on, wherein said sensor policy indicates when to read said first and second sensors according to the physiological characteristic;
acquire a first set of data from said first sensor while data acquisition from said second sensor is turned off;
identify, from the first set of data, a start of an event;
turn on data acquisition from said second sensor according to said sensor policy in response to identifying said start of said event; and
acquire a second set of data from said second sensor.

2. A sensor apparatus as recited in claim 1, wherein the programming is further configured for directing the processor to acquire data from said first sensor and said second sensor over a time frame, and determine said sensor policy from said data from said first sensor and said second sensor over said time frame.

3. A sensor apparatus as recited in claim 1, the array further comprising a third sensor, wherein the programming is further configured for directing the processor to:
acquire data from said first sensor and said third sensor over a time frame;
time-shift said data from said third sensor; and
determine by a comparison of the acquired data from said first sensor and the time-shifted acquired data from said third sensor that data from said first sensor is a predictor of data from said third sensor.

4. A sensor apparatus as recited in claim 1, wherein the programming is further configured for directing the processor to place the second sensor in a sleep mode while data is being acquired from the first sensor.

5. A sensor apparatus as recited in claim 1, wherein the programming is further configured for directing the processor to place the first sensor in a sleep mode while data is being acquired from the second sensor.

6. A sensor apparatus as recited in claim 1:
wherein the array comprises a sensing pad disposed within a sole of a shoe, said physiological characteristic comprising a gait characteristic; and
wherein the programming is further configured for directing the processor to segment a signal from the array according to said gait characteristic.

7. A sensor apparatus as recited in claim 6:
wherein the signal comprises a plantar pressure signal;
wherein the signal is segmented into an airborne segment, a landing segment, and a take-off segment; and
wherein one or more of the first and second sensors are placed in a sleep mode during at least a portion of the airborne segment.

8. A sensor apparatus as recited in claim 1, wherein the sensor policy indicates when to read said first and second sensors based on a known attribute of the physiological characteristic.

9. A sensor apparatus as recited in claim 1, wherein the first sensor and the second sensor are selected predictor sensors of a plurality of sensors, selected according to an ability to predict values of other sensors.

10. A sensor apparatus as recited in claim 1, further configured to direct the processor to detect noise in the first set of data or in the second set of data, and adjust the sensor policy to acquire data from the first sensor and a third sensor different from the first sensor and the second sensor.

11. A sensor apparatus as recited in claim 1, further comprising a third sensor and a fourth sensor, wherein the first sensor and the third sensor together predict values of the fourth sensor, and the programming further configured to direct the processor to turn off sampling of the fourth sensor according to the sensor policy.

* * * * *